US007608074B2

(12) United States Patent
Austin et al.

(10) Patent No.: US 7,608,074 B2
(45) Date of Patent: Oct. 27, 2009

(54) EXTERNAL FIXATION APPARATUS AND METHOD

(75) Inventors: Gene Edward Austin, Bartlett, TN (US); Anthony James, Bartlett, TN (US); Wayne Rankhorn, Rossville, TN (US); Johnny Mason, Memphis, TN (US); Carlos Rodriguez, Gleason, TN (US)

(73) Assignee: Smith & Nephew, Inc., Memphis, TN (US)

( * ) Notice: Subject to any disclaimer, the term of this patent is extended or adjusted under 35 U.S.C. 154(b) by 367 days.

(21) Appl. No.: 10/607,010

(22) Filed: Jun. 26, 2003

(65) Prior Publication Data

US 2004/0138659 A1 Jul. 15, 2004

Related U.S. Application Data

(60) Provisional application No. 60/439,195, filed on Jan. 10, 2003.

(51) Int. Cl.
*A61B 17/00* (2006.01)
(52) U.S. Cl. ....................................... 606/54
(58) Field of Classification Search .............. 606/54, 606/55, 57, 59, 53, 56, 58, 86–89, 96, 99, 606/104, 86 R; 411/516; 403/157, 329, 403/360
See application file for complete search history.

(56) References Cited

U.S. PATENT DOCUMENTS

| 554,284 A | 8/1896 | Lorang |
|---|---|---|
| 575,631 A | 1/1897 | Brooks |
| 1,271,792 A | 7/1918 | Standish |
| 1,563,242 A | 11/1925 | Tweit |
| 2,250,417 A | 7/1941 | Ettinger |
| 2,251,209 A | 7/1941 | Stader |
| 2,346,346 A | 4/1944 | Anderson |
| 2,391,537 A | 12/1945 | Anderson |
| 2,391,693 A | 12/1945 | Ettinger |
| 2,393,694 A | 1/1946 | Kirschner |

(Continued)

FOREIGN PATENT DOCUMENTS

| CH | 303453 | 5/1952 |
|---|---|---|
| CH | 02 709/94-3 | 9/1994 |
| DE | 375 151 | 5/1923 |
| DE | 1 935 977 | 2/1971 |
| DE | 1 603 999 | 5/1971 |
| DE | 27 45 504 A1 | 4/1979 |

(Continued)

OTHER PUBLICATIONS

Hontzsch, et al., 'The New Open Universal Clamp for the External Fixator Tubular System of the AO/ASIF,' *AO/ASIF Dialogue*, VII(1):6-9 (Jun. 1994).
Hontzsch, et al. 'Neue offene Universalbacke fur das Fixateur externe-Rohrsystem der AO,' *Aktuelle Traumatologie*, 24:24-30 (1994).

*Primary Examiner*—Thomas C Barrett
*Assistant Examiner*—James L. Swiger
(74) *Attorney, Agent, or Firm*—Fish & Richardson P.C.

(57) ABSTRACT

Apparatuses and methods for externally fixing and precisely adjusting fractures, such as fractures near the ankle, are disclosed. In one embodiment, an external fixation apparatus includes a first member attachable to a first bone segment through pins, a second member coupled to the first member through a lockable ball joint, wherein first and second ends of the second member may be translated transversely relative to a longitudinal axis of the second member, and a pin clamp coupled to and rotatable about the second member through a lockable joint and attachable to a second bone segment. The pin clamp and the second member may be releasably coupled.

19 Claims, 16 Drawing Sheets

U.S. PATENT DOCUMENTS

| | | | |
|---|---|---|---|
| 2,393,831 A | 1/1946 | Stader | |
| 2,427,128 A | 9/1947 | Ettinger | |
| 2,774,271 A | 12/1956 | Mano | |
| 2,876,027 A | 3/1959 | Sulmonetti | |
| 2,932,029 A | 4/1960 | Nicolo | |
| 3,044,512 A | 7/1962 | Jones | |
| 3,154,331 A | 10/1964 | Engelhardt | |
| 3,195,380 A | 7/1965 | Bicks | |
| 3,509,882 A | 5/1970 | Blake | |
| 3,828,791 A | 8/1974 | Santos | |
| 3,961,854 A | 6/1976 | Jaquet | |
| 4,135,505 A | 1/1979 | Day | |
| 4,170,990 A | 10/1979 | Baumgart et al. | |
| 4,187,840 A | 2/1980 | Watanabe | |
| 4,227,826 A | 10/1980 | Conrad | |
| 4,364,381 A | 12/1982 | Sher et al. | |
| 4,475,546 A | 10/1984 | Patton | |
| 4,483,334 A | 11/1984 | Murray | |
| RE31,809 E | 1/1985 | Danieletto et al. | |
| 4,548,199 A | 10/1985 | Agee | |
| 4,570,625 A | 2/1986 | Harris et al. | |
| 4,611,586 A | 9/1986 | Agee et al. | |
| 4,620,533 A | 11/1986 | Mears | |
| 4,635,634 A | 1/1987 | Santos | |
| 4,666,109 A | 5/1987 | Fallon et al. | |
| 4,696,293 A | 9/1987 | Ciullo | |
| 4,700,437 A | 10/1987 | Hoshino | |
| 4,730,608 A | 3/1988 | Schlein | |
| 4,785,694 A | 11/1988 | Burmester | |
| 4,836,485 A * | 6/1989 | Cooper | 248/278.1 |
| 4,848,368 A | 7/1989 | Kronner | |
| 4,922,856 A | 5/1990 | Sweeney, Jr. | |
| 4,998,935 A | 3/1991 | Pennig | |
| 5,019,077 A * | 5/1991 | De Bastiani et al. | 606/54 |
| 5,062,844 A | 11/1991 | Jamison et al. | |
| 5,152,280 A | 10/1992 | Danieli | |
| 5,160,335 A | 11/1992 | Wagenknecht | |
| 5,167,725 A | 12/1992 | Clark et al. | |
| 5,207,676 A | 5/1993 | Canadell et al. | |
| 5,219,349 A | 6/1993 | Krag et al. | |
| 5,304,177 A | 4/1994 | Pennig | |
| 5,376,090 A | 12/1994 | Pennig | |
| 5,403,313 A | 4/1995 | Lin | |
| 5,405,347 A | 4/1995 | Lee et al. | |
| RE34,985 E | 6/1995 | Pennig | |
| 5,429,637 A | 7/1995 | Hardy | |
| 5,437,666 A | 8/1995 | Tepic et al. | |
| 5,443,465 A | 8/1995 | Pennig | |
| 5,451,225 A | 9/1995 | Ross, Jr. et al. | |
| 5,451,226 A | 9/1995 | Pfeil et al. | |
| 5,507,760 A | 4/1996 | Wynne et al. | |
| 5,545,162 A | 8/1996 | Huebner | |
| 5,586,983 A | 12/1996 | Sanders et al. | |
| 5,622,648 A | 4/1997 | Parri et al. | |
| 5,624,447 A | 4/1997 | Myers | |
| 5,658,283 A | 8/1997 | Huebner | |
| 5,662,648 A | 9/1997 | Facciioli et al. | |
| 5,662,649 A | 9/1997 | Huebner | |
| 5,662,650 A | 9/1997 | Bailey et al. | |
| 5,683,389 A | 11/1997 | Orsak | |
| 5,690,633 A | 11/1997 | Taylor et al. | |
| 5,702,389 A | 12/1997 | Taylor et al. | |
| 5,707,370 A | 1/1998 | Berki et al. | |
| 5,709,685 A | 1/1998 | Dombrowski et al. | |
| 5,728,095 A | 3/1998 | Taylor et al. | |
| 5,728,096 A | 3/1998 | Faccioli et al. | |
| 5,741,252 A | 4/1998 | Mazzio et al. | |
| 5,743,898 A | 4/1998 | Bailey et al. | |
| 5,746,741 A | 5/1998 | Kraus et al. | |
| 5,752,954 A | 5/1998 | Mata et al. | |
| 5,769,851 A * | 6/1998 | Veith | 606/57 |
| 5,788,695 A | 8/1998 | Richardson | |
| 5,810,817 A | 9/1998 | Roussouly et al. | |
| 5,823,486 A | 10/1998 | Smith et al. | |
| 5,827,282 A * | 10/1998 | Pennig | 606/54 |
| 5,891,143 A | 4/1999 | Taylor et al. | |
| 5,891,144 A | 4/1999 | Mata et al. | |
| 5,931,837 A | 8/1999 | Marsh et al. | |
| 5,941,877 A * | 8/1999 | Viegas et al. | 606/55 |
| 5,968,043 A | 10/1999 | Ross et al. | |
| 5,971,984 A | 10/1999 | Taylor et al. | |
| 5,976,134 A | 11/1999 | Huebner | |
| 6,010,501 A | 1/2000 | Raskin et al. | |
| 6,024,745 A | 2/2000 | Faccioli et al. | |
| 6,030,386 A | 2/2000 | Taylor et al. | |
| 6,036,691 A | 3/2000 | Richardson | |
| 6,066,142 A | 5/2000 | Serbousek et al. | |
| 6,080,153 A | 6/2000 | Mata et al. | |
| 6,129,727 A | 10/2000 | Austin et al. | |
| 6,168,595 B1 | 1/2001 | Durham et al. | |
| 6,171,308 B1 | 1/2001 | Bailey et al. | |
| 6,203,575 B1 | 3/2001 | Farey | |
| 6,217,577 B1 | 4/2001 | Hofmann | |
| 6,221,072 B1 | 4/2001 | Termaten | |
| 6,238,400 B1 | 5/2001 | Bays | |
| 6,342,054 B1 | 1/2002 | Mata | |
| 6,386,786 B1 | 5/2002 | Perlman et al. | |
| 6,423,061 B1 * | 7/2002 | Bryant | 606/57 |
| 6,461,358 B1 | 10/2002 | Paccioli et al. | |
| 6,491,694 B1 | 12/2002 | Orsak | |
| 6,503,340 B1 | 1/2003 | Gold et al. | |
| 6,613,049 B2 | 9/2003 | Winquist et al. | |
| 6,616,664 B2 | 9/2003 | Waluik et al. | |
| 6,709,433 B1 | 3/2004 | Schoenefeld | |
| 2002/0026190 A1 | 2/2002 | Walulik et al. | |
| 2002/0077629 A1 * | 6/2002 | Hoffman et al. | 606/59 |
| 2003/0149429 A1 | 8/2003 | Ferrante et al. | |
| 2003/0149430 A1 | 8/2003 | Ferrante et al. | |
| 2005/0245939 A1 | 11/2005 | Ferrante et al. | |

FOREIGN PATENT DOCUMENTS

| | | |
|---|---|---|
| DE | 38 05 178 A1 | 8/1989 |
| DE | 38 23 746 A1 | 1/1990 |
| DE | 42 38 582 A1 | 5/1994 |
| DE | 295 12 917 | 11/1995 |
| EP | 0 524 441 A1 | 6/1992 |
| EP | 0 611 007 A1 | 8/1994 |
| EP | 0 700 664 A1 | 3/1996 |
| EP | 1 021 992 A1 | 7/2000 |
| FR | 2 665 353 A | 2/1992 |
| NO | 25934 | 6/1915 |
| RU | 1572590 A1 | 9/1994 |
| SU | 167008 | 11/1965 |
| SU | 1491-492 A1 | 8/1986 |
| WO | WO 88/01152 | 2/1988 |
| WO | WO 88/03395 | 5/1988 |
| WO | WO 94/18898 | 9/1994 |
| WO | WO 96/12443 | 5/1996 |
| WO | WO 97/10775 | 3/1997 |
| WO | WO 97/16128 | 5/1997 |
| WO | WO 98/36698 | 8/1998 |
| WO | WO 99/22661 | 5/1999 |
| WO | WO 99/29247 | 6/1999 |
| WO | WO 00/40163 | 7/2000 |
| WO | WO 03/065911 | 8/2003 |
| WO | WO 03/105704 A1 | 12/2003 |
| WO | WO 2004/062514 A1 | 7/2004 |
| WO | WO 2006/007553 A2 | 1/2006 |

* cited by examiner

EXTERNAL FIXATION APPARATUS AND METHOD

RELATED APPLICATIONS

This application claims the benefit of U.S. Provisional Application Ser. No. 60/439,195, entitled "External Fixation Apparatus and Method," filed Jan. 10, 2003, the entire contents of which are hereby incorporated by reference.

FIELD OF THE INVENTION

The invention relates generally to apparatuses and methods of orthopedic external fixation, and, more particularly, to apparatuses and methods for externally fixing and precisely adjusting fractures, such as fractures near the ankle.

BACKGROUND OF THE INVENTION

External fixation of fractures has been practiced extensively, and there exists a number of external fixation devices designed to fix fractures of the ankle. Generally, these devices attach to the tibia with bone pins, span the fracture, and attach to bones of the foot, the talus and calcaneus, to secure the fracture while it heals. Some of the devices are designed to provide a pivot point in the external fixator adjacent to the natural hinge point of the patient's ankle. It is suggested by some that allowing the external fixator and ankle to pivot at some times during the healing process is advantageous. This view is not held by all, and some of the external fixators are not designed to pivot in this manner, or are designed to be lockable to selectively inhibit any pivoting prior to healing. Some external fixators are also adjustable longitudinally.

However, none of the existing external fixation devices are capable of adjustment and consequent fine adjustment of a fracture reduction lateral or transverse to the longitudinal axis of a fixator once the fixator has been placed on the bone pins and tightened. Therefore, if any transverse fracture reduction adjustment is needed, the fixator must be loosened, the fracture realigned, and the fixator tightened again. Prior devices also fail to give significant flexibility in pin placement and orientation in the foot of a patient. It is important that external fixation devices for the ankle be easier to use, less cumbersome, and more versatile than existing devices, particularly when used in a trauma setting.

Accordingly, there is a need for apparatuses and methods optimized to enable convenient placement and locking of an external fixator and apparatuses and methods that provide for fine adjustment of fracture reduction without requiring loosening of the external fixator. It would be additionally advantageous to enable manipulation of the external fixator in greater degrees of freedom in order to more effectively and efficiently place fixation elements such as bone pins. Furthermore, it would be advantageous in certain embodiments to provide for rotatable removal and attachment means for multiple fixator configurations.

All of these are particularly important in the context of ankle fixators, even though it is possible for concepts, features, and aspects of the invention, and embodiments of it, to be used in the context of other points in the human body.

SUMMARY OF THE INVENTION

The present invention provides apparatuses and methods for externally fixing and precisely adjusting fractures in or near a joint, such as fractures near the ankle. According to an exemplary embodiment of this invention, an external fixation apparatus includes a first member attachable to a first bone segment through pins, a second member coupled to the first member through a lockable ball joint, wherein first and second ends of the second member may be translated transversely relative to a longitudinal axis of the second member, and a pin clamp coupled to and rotatable about the second member through a lockable joint and attachable to a second bone segment. The first bone segment may be a tibia and the second bone segment may be a talus or a calcaneus. The second member may include a unitary, bifurcated, or other type of stem. The pin clamp may be symmetrical or asymmetrical.

According to certain exemplary embodiments, translation of first and second ends of a second member relative to the longitudinal axis of the second member is possible in at least two dimensions. In one embodiment, the second member includes a carriage that fits within an upper recess and a lower recess of the second member, the carriage including two threaded holes each for receiving a worm gear, and keybolts for operating each worm gear such that the carriage may be moved transversely to the longitudinal axis in one dimension within the upper recess and transversely relative to the longitudinal axis in another dimension within the lower recess.

According to one embodiment of this invention, a lockable joint coupling a second member and a pin clamp includes an axle extending through a hole in a first jaw of the pin clamp and a hole in the second end of the second member, an anti-rotation pin inserted through a portion of the second member and into the axle, and a first bolt that passes through openings in first and second jaws of the pin clamp such that tightening of the first bolt interferes with the axle and locks rotation of the pin clamp and the second member.

According to another embodiment of this invention, a lockable joint coupling a second member and a pin clamp includes a threaded sleeve fixed to the second member and a core with internal hex driving sockets that is threaded onto the sleeve so that as the core is moved along the sleeve, balls are forced up ramps and into the pin clamp or allowed to move down ramps and away from the pin clamp.

According to another embodiment of this invention, a lockable joint coupling a second member and a pin clamp includes a biasing element and a pushbutton core contacting the biasing element such that when the pushbutton core is depressed the pin clamp may rotate freely.

According to another embodiment of this invention, a lockable joint coupling a second member and a pin clamp includes a shaft extending transversely from the second end of the second member, the shaft including at least one circumferential groove, a hole within a first jaw of the pin clamp that receives the shaft, a locator pin of the pin clamp that is received within the at least one circumferential groove to releasably couple the second member and the pin clamp, and a first bolt that passes through openings in the first jaw and a second jaw of the pin clamp such that tightening of the first bolt interferes with the shaft and locks rotation of the pin clamp and the second member.

According to certain exemplary embodiments of this invention, a lockable joint coupling a second member and a pin clamp provides for multi-axis rotation between the second member and the pin clamp.

In one embodiment of this invention, a lockable joint coupling a second member and a pin clamp includes a sphere suspended from the second end of the second member that is received within interior surfaces of first and second jaws of the pin clamp and at least one bolt that passes through openings in at least one of the first and second jaws of the pin clamp such that tightening of the at least one bolt interferes with the sphere and locks rotation of the pin clamp and the second member.

In another embodiment of this invention, a lockable joint coupling a second member and a pin clamp includes a sphere attached to the pin clamp and a compression bolt that extends through holes in the sphere of the pin clamp and the second member so that when the bolt is tightened with a lock nut, the second member is compressed against the sphere thereby locking rotation of the second member and the pin clamp.

In another embodiment of this invention, a lockable joint coupling a second member and a pin clamp includes a connector that is held within a sphere-shaped tip of the second member by a retaining cap and a biasing element, the connector having a ball end and a threaded end, a cooperating surface of the pin clamp that receives the sphere-shaped tip of the second member and the threaded end of the connector, and a nut that is threaded onto the threaded end of the connector to retain the connector within the pin clamp and such that when the nut is tightened the sphere-shaped tip of the second member and the cooperating surface of the pin clamp are locked against one another.

In another embodiment of this invention, a lockable joint coupling a second member and a pin clamp includes a connector held within a sphere-shaped tip of the pin clamp, a cooperating surface of the second member that receives the sphere-shaped tip of the pin clamp and a shaft end of the connector, and a wedge bolt extending through the second member that is tightened by a wedge nut causing a ramp to force a ball end of the connector to be pulled up forcing the sphere-shaped tip of the pin clamp and the cooperating surface of the second member to lock against one another.

In another embodiment of this invention, a lockable joint coupling a second member and a pin clamp includes two stacked washers attached to a spherical portion of the second member, two stacked washers attached to the pin clamp, wherein the two stacked washers of the pin clamp are alternatingly nested with the two stacked washers of the second member, and a bolt extending from the pin clamp and into the spherical portion of the second member such that all of the washers and the spherical portion are pressed together upon tightening of the bolt, thereby locking rotation of the pin clamp and the second member.

According to certain exemplary embodiments of the present invention, a second member may be biased at its second end from the longitudinal axis of the second member up to approximately sixty degrees.

According to certain exemplary embodiments of this invention, an external fixation apparatus includes a first member attachable to a first bone segment through pins, a second member coupled to the first member through a lockable joint, the second member including a shaft extending transversely from a distal end of the second member with at least one circumferential groove in the shaft, and a pin clamp attachable to a second bone segment and releasably coupled to and rotatable about the second member. The pin clamp may include a first jaw and a second jaw, the first jaw including a hole that receives the shaft, a locator pin that is received within the at least one circumferential groove of the shaft to releasably couple the second member and the pin clamp, and a first bolt that passes through openings in the first and second jaws such that tightening of the first bolt interferes with the shaft and locks rotation of the pin clamp and the second member. The locator pin may be configured to allow for pull release or pushbutton release of the second member from the pin clamp. The pin clamp may include second and third bolts that hold the first and second jaws together and attach and clamp pins or wires to the second bone segment, and the first and second jaws may include openings that receive biasing elements and threaded ends of the second and third bolts.

According to certain exemplary embodiments of this invention, an external fixation system for attaching pins or wires to at least one bone segment includes an external fixation device and a pin clamp. The pin clamp may include a first jaw and a second jaw, biasing elements received within openings in the first and second jaws, first and second bolts that extend through the openings in the first and second jaws, compressing the biasing elements and holding the first and second jaws together, a hole in the first jaw that receives a shaft of an external fixation device, the shaft having at least one circumferential groove, a locator pin that is received within the at least one circumferential groove of the shaft to releasably couple the external fixation device and the pin clamp, and a third bolt that passes through openings in the first and second jaws such that sufficient tightening of the third bolt interferes with the shaft and locks rotation of the pin clamp and the external fixation device. In one embodiment, the external fixation device is a handle such that the pin clamp and handle coupled thereto may be used as a drill guide. In another embodiment, the external fixation device is a fixation component that includes a capture member that receives a pin, bar, or wire. In another embodiment, the external fixation device is a second member with first and second ends that may be translated transversely in at least two dimensions relative to a longitudinal axis of the second member.

Certain exemplary embodiments of this invention also include methods of reducing a fracture.

BRIEF DESCRIPTION OF THE DRAWINGS

FIG. 17 is an exploded, cross-sectional elevation view of the embodiment of the external fixation apparatus shown in FIG. 16.

DETAILED DESCRIPTION OF THE INVENTION

Figure 1:
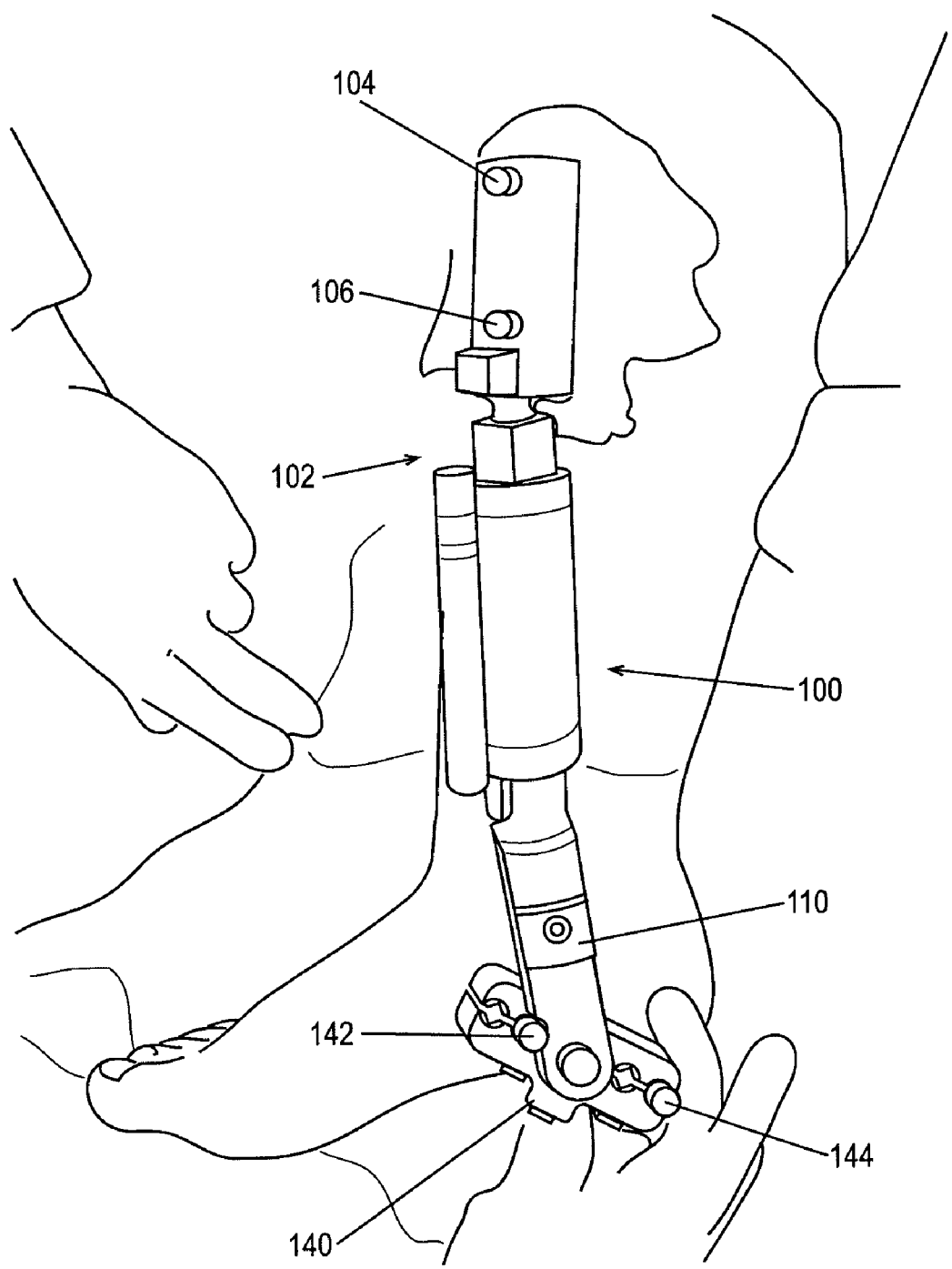
FIG. 1 is a perspective view of an embodiment of an apparatus according to the present invention in use to support the ankle of a patient.

FIG. 1 shows an external fixation apparatus 100 placed on the lower leg and ankle of a human. External fixation apparatus 100 includes a first member 102 that is attached to a tibia through upper bone pins 104 and 106. As shown in FIG. 1, first member 102 includes upper and lower components that cooperate to provide for additional adjustments, but first member 102 may be a single component. A second member 110, sometimes referred to in practice as a pivot arm or a stem, is coupled to first member 102 through a lockable joint, preferably a ball joint. A pin clamp 140, sometimes referred to in practice as a pin block, is coupled to second member 110 and to a second bone segment through lower bone pins 142 and 144. A first lower bone pin 142 may be attached to the talus and a second lower bone pin 144 may be attached to the calcaneus, as shown more clearly in FIG. 2. The talus and calcaneus are both bones of the foot and semi-rigidly fixed to one another through tissues of the foot, and therefore may be considered as a unitary bone segment for the purpose of the invention and referred to as a bone segment herein. Similarly, other combinations of the skeletal structure may be considered a bone segment for purposes of the invention. Although pin clamp 140 and bone pins 102, 104, 142, and 144 are designated as "pin" or "pins," other devices capable of fixing to skeletal structures, such as, but not limited to, wires, are within the scope of fixation systems and devices available for use with certain exemplary embodiments of the present invention.

Figure 2:
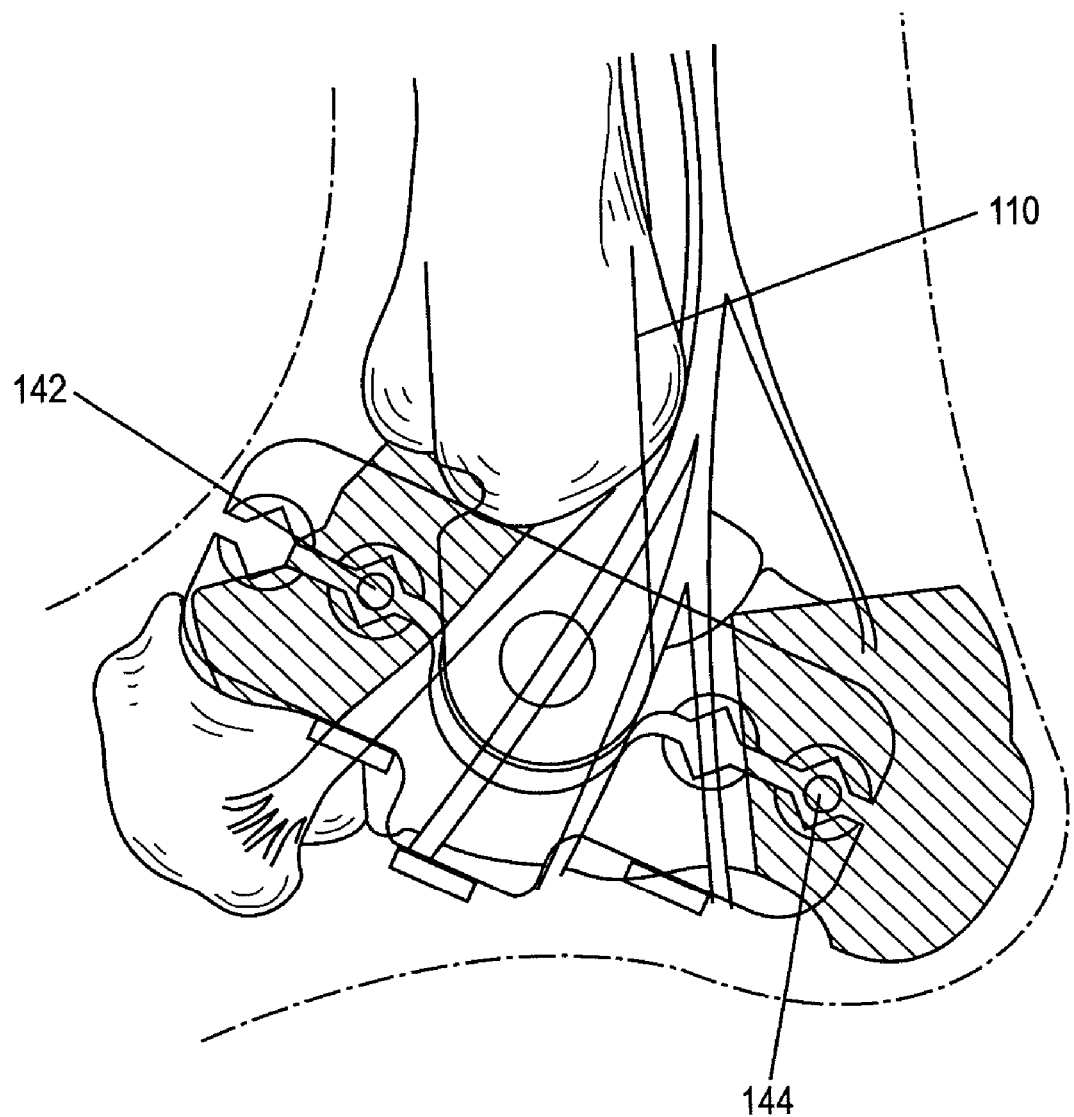
FIG. 2 shows the alignment of an embodiment of a pin clamp according to the present invention over the ankle of a patient.

FIG. 2 illustrates the typical placement of pin clamp 140 on the anatomy of a patient. As noted above, first lower bone pin 142 is attached to the talus and second lower bone pin 144 is attached to the calcaneus. As shown in FIG. 2, pin clamp 140 is symmetrical. However, pin clamp 140 may be asymmetrical, such as, for example, pin clamp 340 shown in FIG. 15. Pin clamp 140 may be pivoted about the second member 110, as further described below, and used interchangeably from either the left or the right side of the leg of a patient. As shown in FIG. 2, first lower bone pin 142 is closer to an axle 112 that goes through the center of pin clamp 140 than is second lower bone pin 144.

Figure 3:
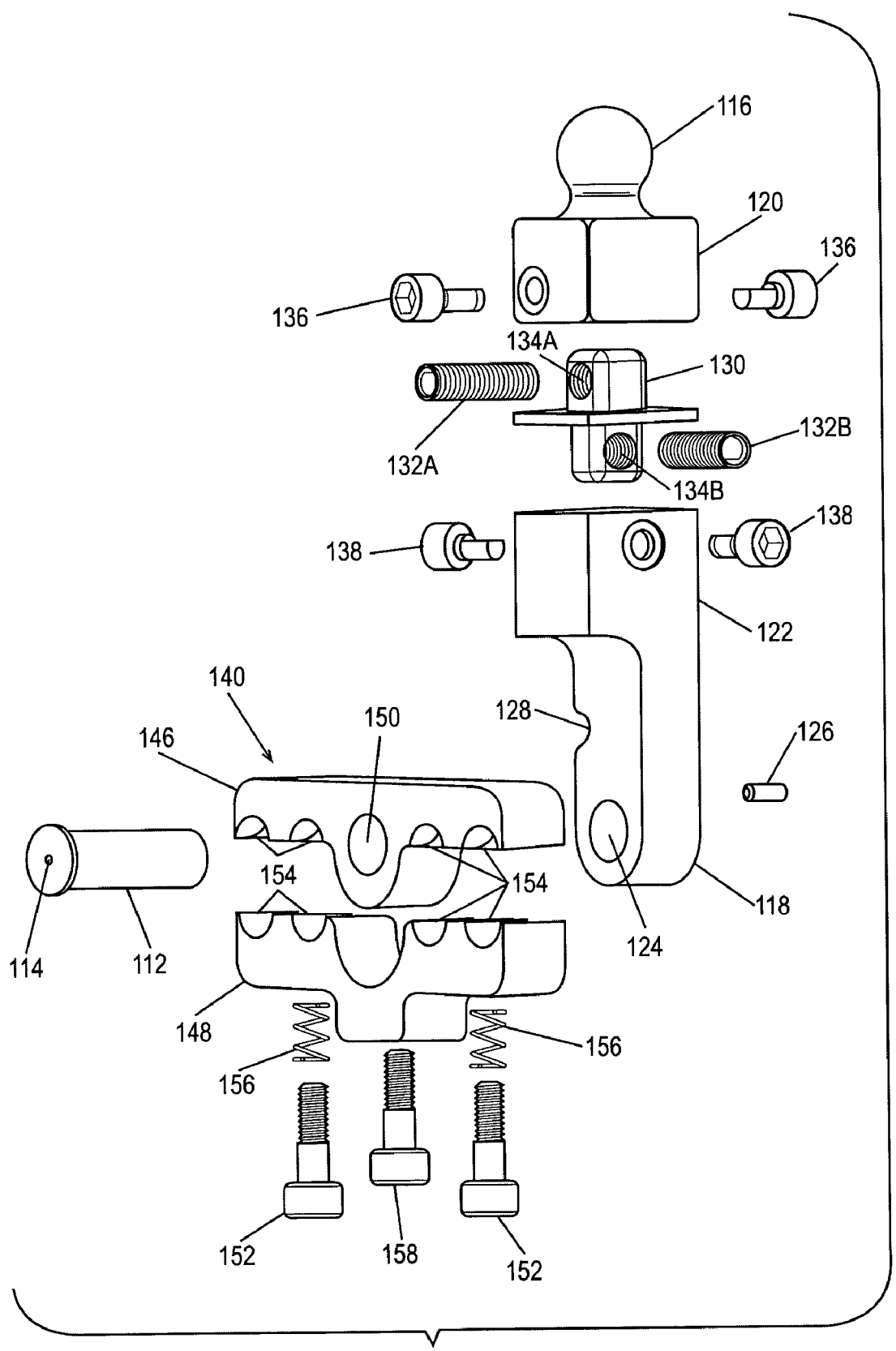
FIG. 3 is an exploded perspective view of components of an embodiment of an apparatus according to the present invention.

FIG. 3 is an exploded perspective view of components of an embodiment of an external fixation apparatus according to the present invention, including second member 110 and pin clamp 140. Opposite ends 116 and 118 of second member 110 may be translated transversely relative to the longitudinal axis of the second member through use of a carriage 130. Carriage 130 fits within recesses in an upper portion 120 and a lower portion 122 of second member 110. The recesses in portions 120 and 122 of second member 110 are larger than the parts of carriage 130 that fit within the recesses. Therefore, carriage 130 is allowed to move within the recesses laterally along the longitudinal axis of second member 110. A worm gear 132A engages a threaded hole 134A in the upper portion of carriage 130. The length of worm gear 132A fits within the recess in upper portion 120 of second member 110. A keybolt or keybolts 136 may be mated to either or both ends of worm gear 132A to enable worm gear 132A to be operated with an internal hex driver. Operation of worm gear 132A moves carriage 130 laterally between the extents to which carriage 130 is allowed to move within the recess in upper portion 120 of second member 110. More specifically, turning of worm gear 132A within hole 134A will move end 118 either medially or laterally relative to the longitudinal axis of second member 110 and end 116, depending on the direction in which worm gear 132A is turned. Similarly, FIG. 3 shows another worm gear 132B engaged with another threaded hole 134B in the lower portion of carriage 130 such that keybolts 138 may be operated with an internal hex driver. Turning of worm gear 132B within hole 134B will move end 116 either posterior or anterior relative to the longitudinal axis of second member 110 and end 118, depending on the direction in which worm gear 132B is turned.

In certain other exemplary embodiments of the transverse movement feature, finely controlled movement, such as with the two worm gears, may or may not be incorporated. For example, in some embodiments opposite ends of second member 110 would be moveable as a result of a releasable connection within second member 110. The releasable connection could be unlocked, the transverse movement accomplished, and then the connection locked to hold the desired movement. Locking could be accomplished through use of a setscrew. Other apparatuses that would provide finely controlled movement may be used as well. A single worm gear could be used to provide fine adjustment only in the most advantageous dimension. Automated adjustments using mechanical, electrical, thermal, and/or computer-controlled signals or actuators could also be employed. Any apparatus providing for adjustment substantially transverse to the longitudinal axis of the second member 110 is contemplated by certain exemplary embodiments of this invention.

Returning to FIG. 3, pin clamp 140 is coupled to second member 110 through axle 112. Pin clamp 140 includes a first jaw 146 and a second jaw 148. First jaw 146 has a hole 150 through which axle 112 is inserted, and pin clamp 140 is able to rotate about axle 112. Axle 112 is coupled to second member 110 through a hole 124 in second member 110. Axle 112 may be fixed to second member 110 by inserting an anti-rotation pin 126 through a portion of second member 110 and into axle 112. Alternatively, axle 112 could be fixed to second member 110 with an adhesive, by welding, by compression fit, by being formed integrally with second member 110, or by any other method adequate to form a structurally sufficient connection. Axle 112 may also include an alignment hole 114 through which a pin or wire may be placed into the bone. Such alignment may be useful to approximate a desired center of rotation of pin clamp 140. For example, a wire may be placed through alignment hole 114 and into the talus to approximate the pivot axis of a patient's ankle. Second member 110 may also include a notch 128 to provide for additional rotational freedom of pin clamp 140. Notch 128 effectively gives pin clamp 140 a greater range of motion without significantly reducing the strength of second member 110.

First jaw 146 and the second jaw 148 are held together by clamp bolts 152. Clamp bolts 152 may serve to both hold the jaws together, and to attach and clamp bone pins 142 and 144 to a bone segment (see FIG. 1). Bone pins may be clamped in any of the four holes defined by the eight depressions 154, as shown in FIG. 3. Clamp bolts 152 may be urged by biasing elements, such as springs 156, such that first jaw 146 and second jaw 148 tend to push together to stay loosely secured to bone pins prior to tightening clamp bolts 152. A lock bolt 158 may be provided to lock the rotation between second member 110 and pin clamp 140. Lock bolt 158 passes through holes in second jaw 148 and first jaw 146 such that by sufficiently tightening lock bolt 158, the distal end of the bolt interferes with axle 112 and locks rotation between second member 110 and pin clamp 140. As shown in FIG. 3, the threaded hole with which lock bolt 158 engages is in first jaw 146.

Figure 4:
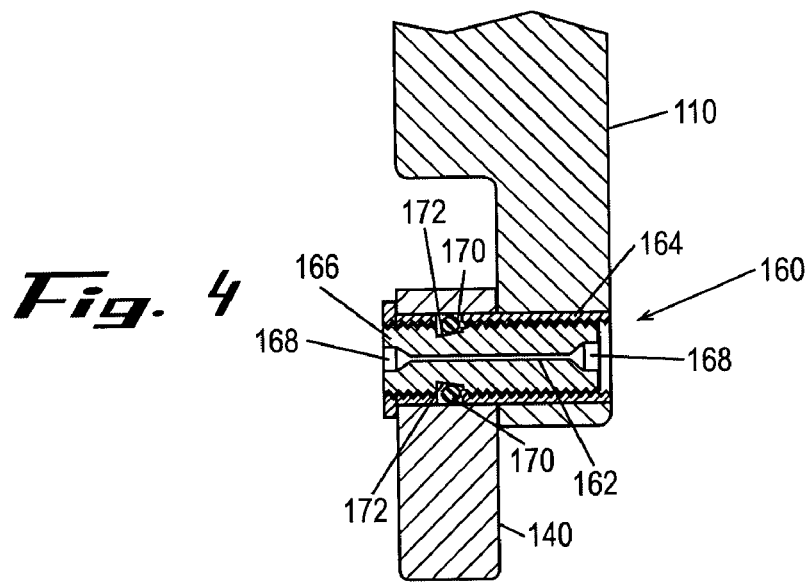
FIG. 4 is a cross-sectional elevation view of an embodiment of a coupling between a second member and a pin clamp according to this invention.
Figure 5:
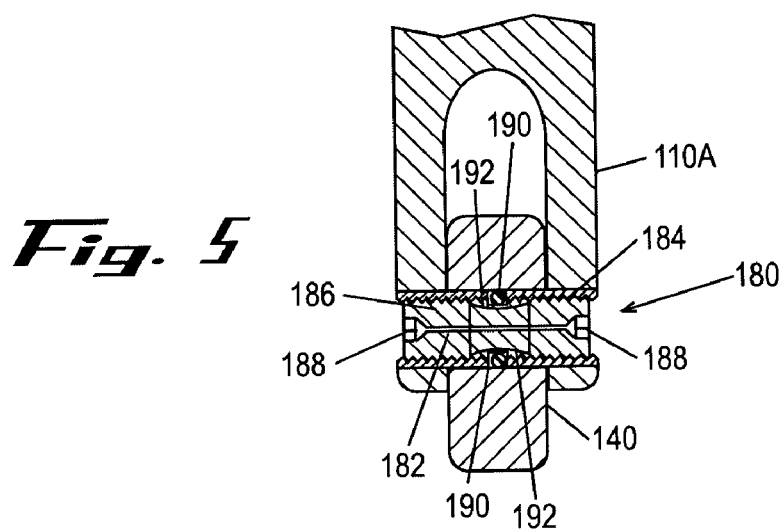
FIG. 5 is a cross-sectional elevation view of another embodiment of a coupling between a second member and a pin clamp according to this invention.
Figure 6:
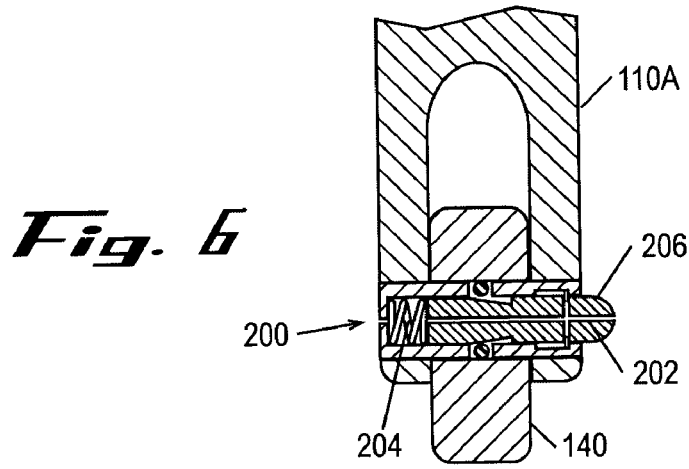
FIG. 6 is a cross-sectional elevation view of another embodiment of a coupling between a second member and a pin clamp according to this invention.

Certain additional exemplary embodiments of coupling between a second member and a pin clamp according to the present invention are shown in FIGS. 4-11. FIGS. 4-6 illustrate configurations useful in locking single axis rotation between a second member and a pin clamp, while FIGS. 7-11 show locking of multi-axis rotation between a second member and a pin clamp. The apparatuses of FIGS. 2, 4, 7, and 9-11 illustrate a second member with a unitary stem to which the pin clamp attaches. The apparatuses of FIGS. 5, 6, and 8 show a second member with a bifurcated stem to which the pin clamp attaches (i.e., two separate appendages of the stem extend to and connect with the pin clamp). As understood by those skilled in the art, the locking mechanisms of the two types of stems may be interchangeable, and merely because a locking mechanism of one type is shown with a stem of a particular type, that does not preclude use with a stem of another type.

FIG. 4 is a cross-sectional elevation view of an embodiment of a coupling between a second member and a pin clamp according to this invention. FIG. 4 shows a single-ramp locking axle 160 useful in locking the coupling between second member 110 and pin clamp 140. Single-ramp locking axle 160 may include an alignment hole 162 for aiding with the placement of the apparatus as described above. Single-ramp locking axle 160 has a threaded sleeve 164 and a core 166 with internal hex driving sockets 168. Core 166 is threaded into sleeve 164, and sleeve 164 is fixed to second member 110. By turning core 166, the core moves along sleeve 164, and balls 170 are forced up or allowed to move down ramps 172 and into or away from pin clamp 140. Balls 170 may therefore be used to lock and unlock movement between second member 110 and pin block 140. Balls 170 and surfaces of pin clamp 140 and ramps 172 may be coated or manufactured such that higher coefficients of friction are generated to enhance the locking. Ramps 172 may be discrete ramps holding a single ball 170, or may be substantially continuous about the exterior of core 166. For example, the surface of core 166 may be a conical shape providing for ramps all around the core.

FIG. 5 is a cross-sectional elevation view of another embodiment of a coupling between a second member and a pin clamp according to this invention. FIG. 5 illustrates a double-ramp locking axle 180 that is similar in function to single-ramp locking axle 160 shown in FIG. 4, but may be tightened by advancing a core 186 in either direction relative to a threaded sleeve 184. Alignment hole 182, internal hex driving sockets 188, balls 190, and ramps 192 are also included. Double-ramp locking axle 180 is shown in use with a bifurcated second member 110A and pin clamp 140.

FIG. 6 is a cross-sectional elevation view of another embodiment of a coupling between a second member and a pin clamp according to this invention. A pushbutton locking axle 200 is shown in FIG. 6. Pushbutton locking axle 200 includes an alignment hole 202. A biasing element 204 is used to keep pushbutton locking axle 200 in a locked configuration unless a pushbutton core 206 is pushed toward biasing element 204. Pushbutton locking axle 200 is shown in use with a bifurcated second member 110A and pin clamp 140.

FIGS. 7-11 illustrate configurations useful in locking multi-axis rotation between a second member and a pin clamp according to this invention. Multi-axis rotation is sometimes useful in giving a user of certain exemplary embodiments of an external fixation apparatus according to this invention flexibility in placement of bone pins or other bone connection devices. Multi-axis rotation may also be useful to adjust fracture reduction. All sphere, ball, spacer, and plate surfaces, and the surfaces that mate therewith may be coated or manufactured such that higher coefficients of friction are generated to enhance the locking described in conjunction with FIGS. 7-11.

Figure 7A:
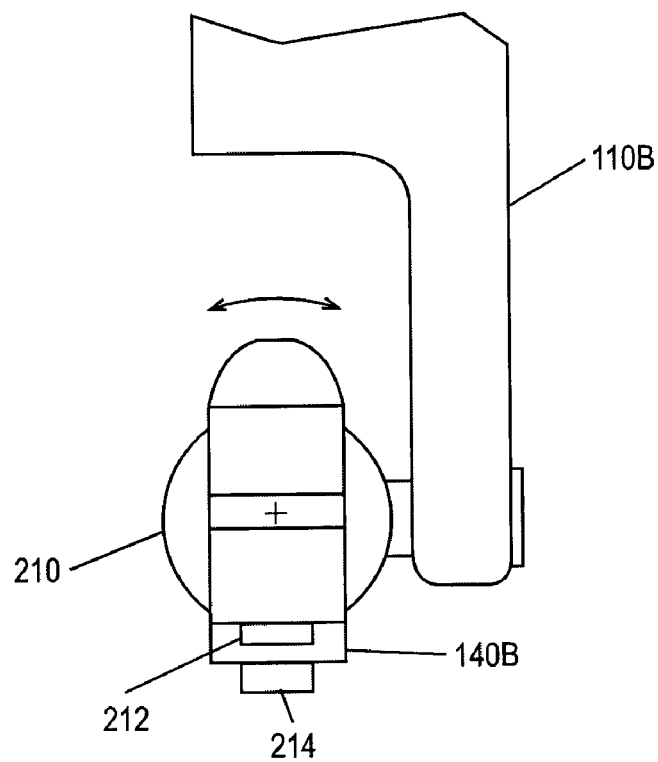
FIGS. 7A and 7B are elevation views of another embodiment of a coupling between a second member and a pin clamp according to this invention.
Figure 7B:
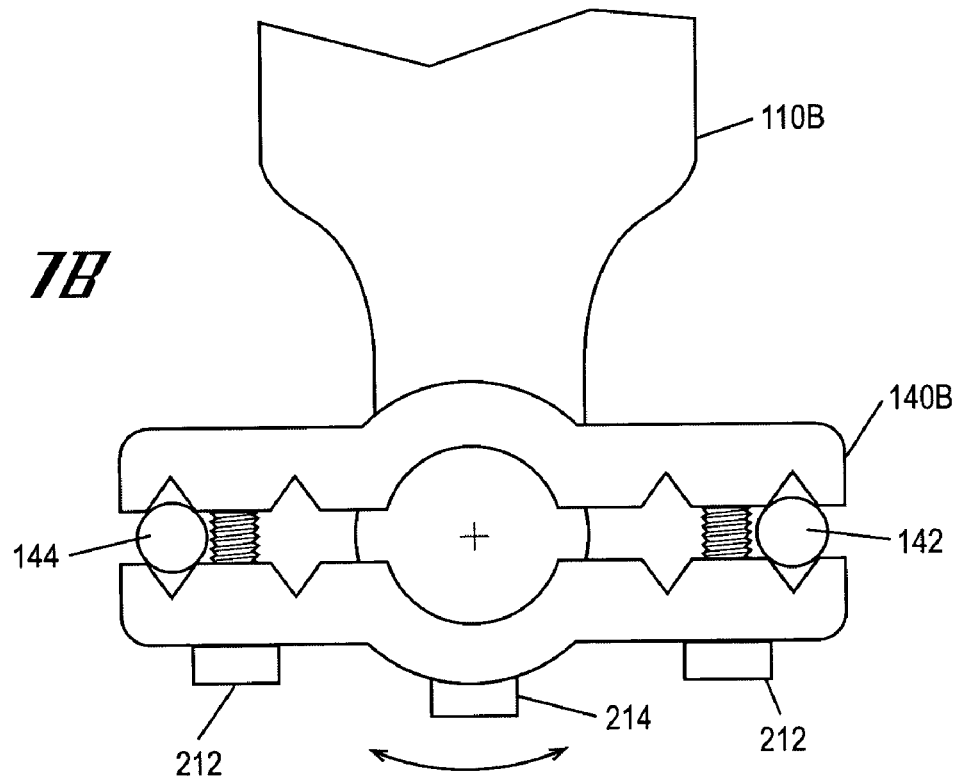

FIGS. 7A and 7B are elevation views of another embodiment of a coupling between a second member and a pin clamp according to this invention. FIGS. 7A and 7B show a sphere 210 suspended from a unitary second member 110B. A pin clamp 140B has interior surfaces that fit around sphere 210 and press against sphere 210 when bolts 212 are tightened. The tightening of bolts 212 therefore may be used to lock pin clamp 140B to both lower bone pins 142 and 144 and sphere 210. Additionally, a sphere locking bolt 214 may be used to lock pin clamp 140B to sphere 210 by tightening sphere locking bolt 214 into contact with sphere 210 through a threaded hole in pin clamp 140B.

Figure 8A:
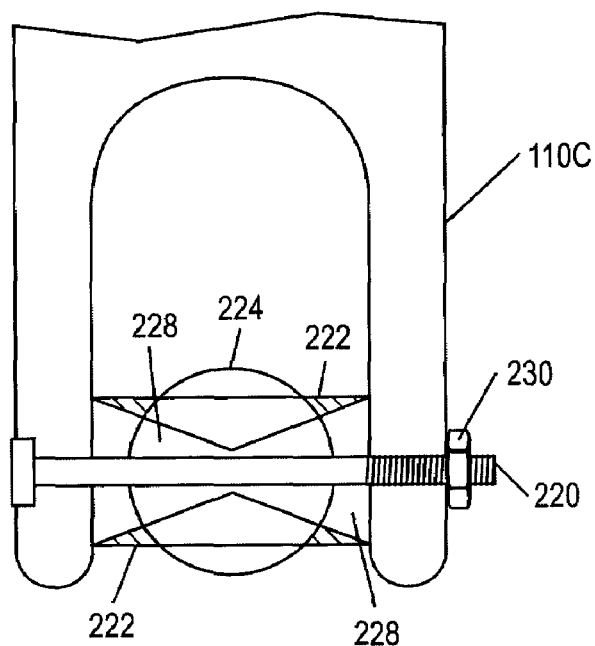
FIGS. 8A and 8B are elevation views of another embodiment of a coupling between a second member and a pin clamp according to this invention.
Figure 8B:
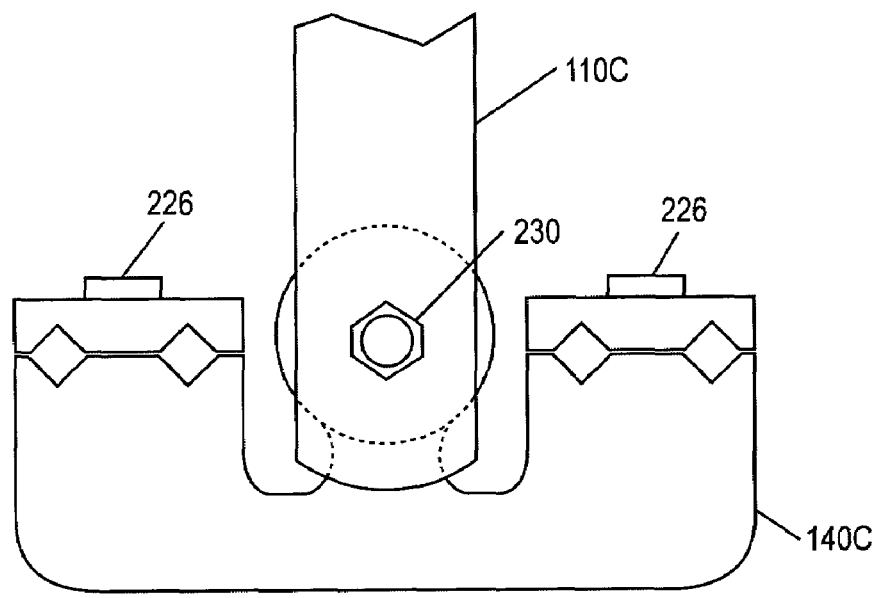

FIGS. 8A and 8B are elevation views of another embodiment of a coupling between a second member and a pin clamp according to this invention. FIGS. 8A and 8B illustrate a compressing, bifurcated second member 110C designed to have its bifurcated appendages pulled together by a compression bolt 220 or a similar connector. The appendages may be pulled into spacers 222 that bear on sphere 224 and lock relative movement between bridging pin clamp 140C and compressing, bifurcated second member 10C. Bolts 226 may be used to attach and lock the bridging pin clamp 140C onto lower bone pins. Sphere 224 and spacers 222 include cutouts 228 to enable rotation of the bridging pin clamp 140C about the axis perpendicular to the plane in which FIG. 8A is drawn. Ball lock nut 230 may also be used.

Figure 9:
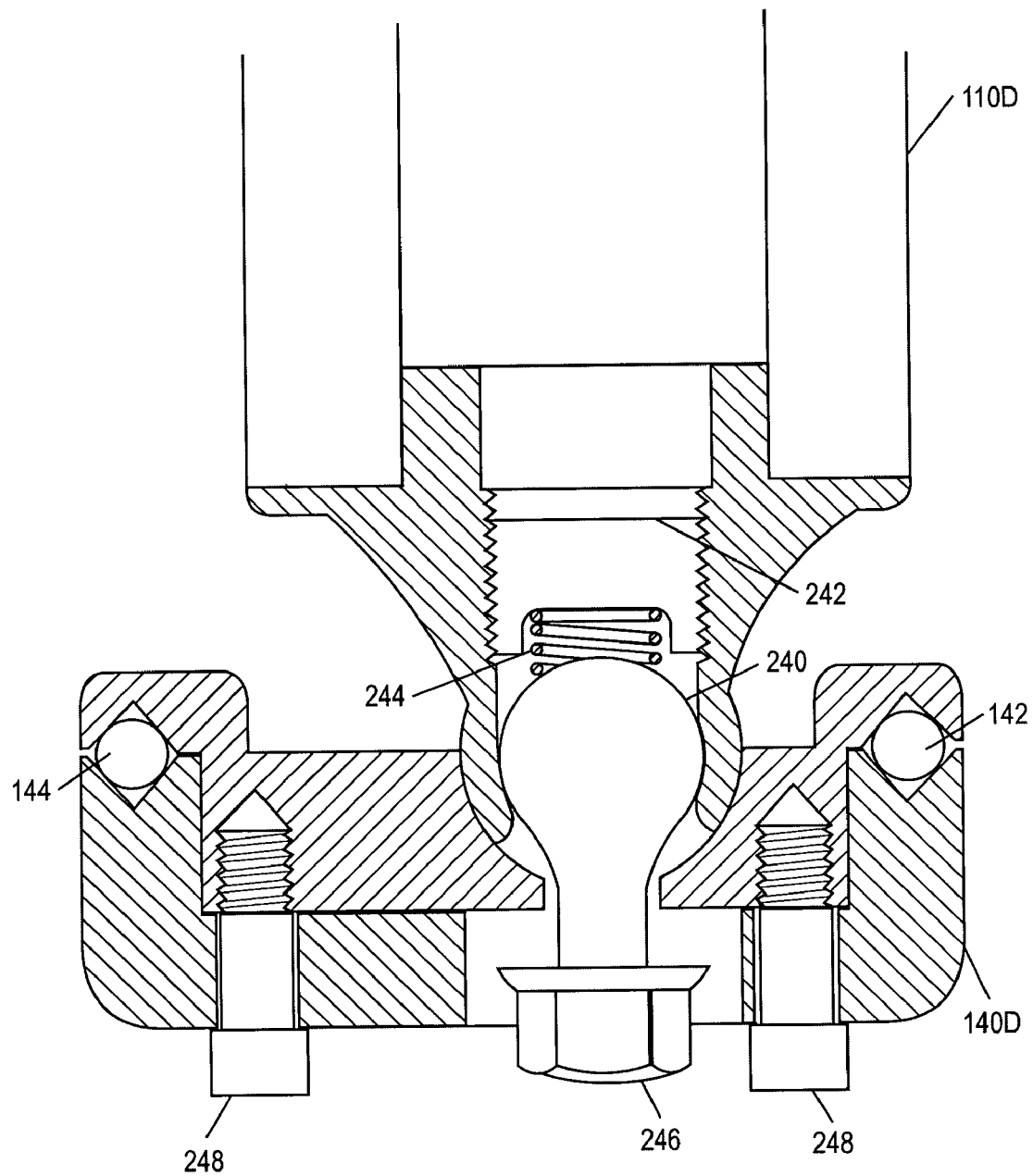
FIG. 9 is a cross-sectional elevation view of another embodiment of a coupling between a second member and a pin clamp according to this invention.

FIG. 9 is a cross-sectional elevation view of another embodiment of a coupling between a second member and a pin clamp according to this invention. FIG. 9 shows a sphere-tipped second member 110D coupled to a nested pin clamp 140D. The nested pin clamp 140D may be bolted to the end of a connector 240 that allows multi-axis rotation between nested pin clamp 140D and sphere-tipped second member 110D. As shown, connector 240 is held in place in sphere-tipped second member 110D by a retaining cap 242 and a spring 244. Connector 240 may therefore rotate about three axes within a useful range. Nested pin clamp 140D fits over the threaded end of connector 240 and is retained by a nut 246. When nut 246 is tightened, the cooperating spherical surfaces of nested pin clamp 140D and sphere-tipped second member 110D are locked against one another. Bolts 248 may be tightened to compress the top and bottom portions of pin clamp 140D and thereby attach lower bone pins 142 and 144.

Figure 10:
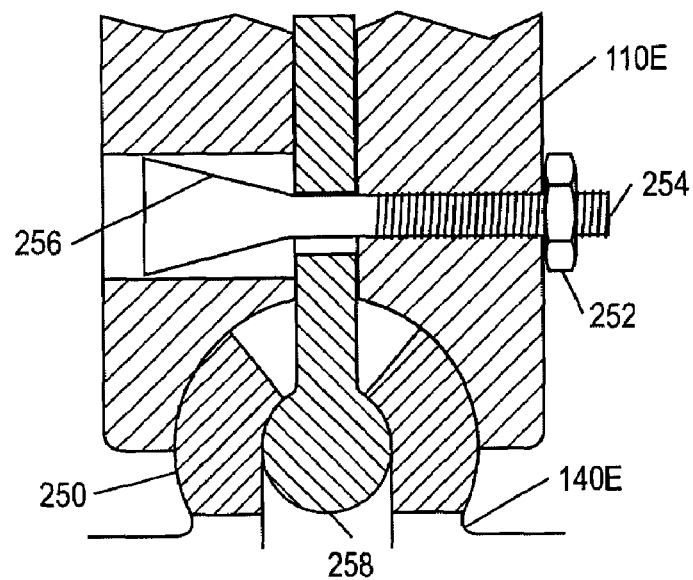
FIG. 10 is a cross-sectional elevation view of another embodiment of a coupling between a second member and a pin clamp according to this invention.

FIG. 10 is a cross-sectional elevation view of another embodiment of a coupling between a second member and a pin clamp according to this invention. FIG. 10 shows a sphere-indented second member 110E engaging a sphere-tipped pin clamp 140E including hollowed sphere 250. Tightening a wedge nut 252 on a wedge bolt 254 causes a ramp 256 to force a lock ball 258 to be pulled up to force the spherical surfaces of the sphere-shaped tip of the pin clamp and the cooperating surfaces of sphere-indented second member 110E to lock against one another. Ramp 256 may be an incline resulting from a conically shaped bolt at any rotational orientation or may be inclined on only the operative side that bears against the shaft of lock ball 258.

Figure 11:
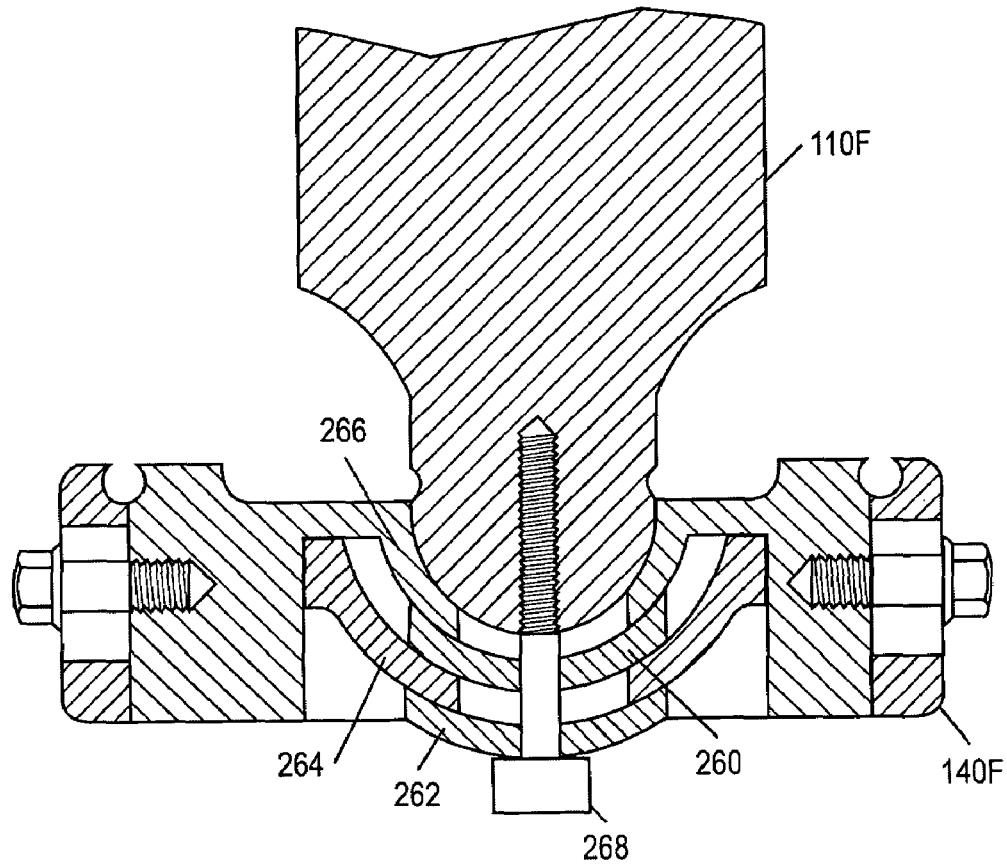
FIG. 11 is a cross-sectional elevation view of another embodiment of a coupling between a second member and a pin clamp according to this invention.

FIG. 11 is a cross-sectional elevation view of another embodiment of a coupling between a second member and a pin clamp according to this invention. FIG. 11 shows a stacked washer second member 110F engaging a stacked washer pin clamp 140F. Out of the plane of FIG. 11, stem stacked washers 260 and 262 are fixed to and a part of the stacked washer second member 110F. Stem stacked washers 260 and 262 and the spherical surface of stacked washer second member 110F nest among the block stacked washers 264 and 266. Consequently, stacked washer second member 110F is able to move about three axes relative to the stacked washer pin clamp 140F. When washer-locking bolt 268 is tightened, washers 260, 262, 264, and 266, and the spherical surface of the stacked washer second member 110F are pressed together and friction on the various surfaces locks movement of the second member and pin clamp.

Figure 12:
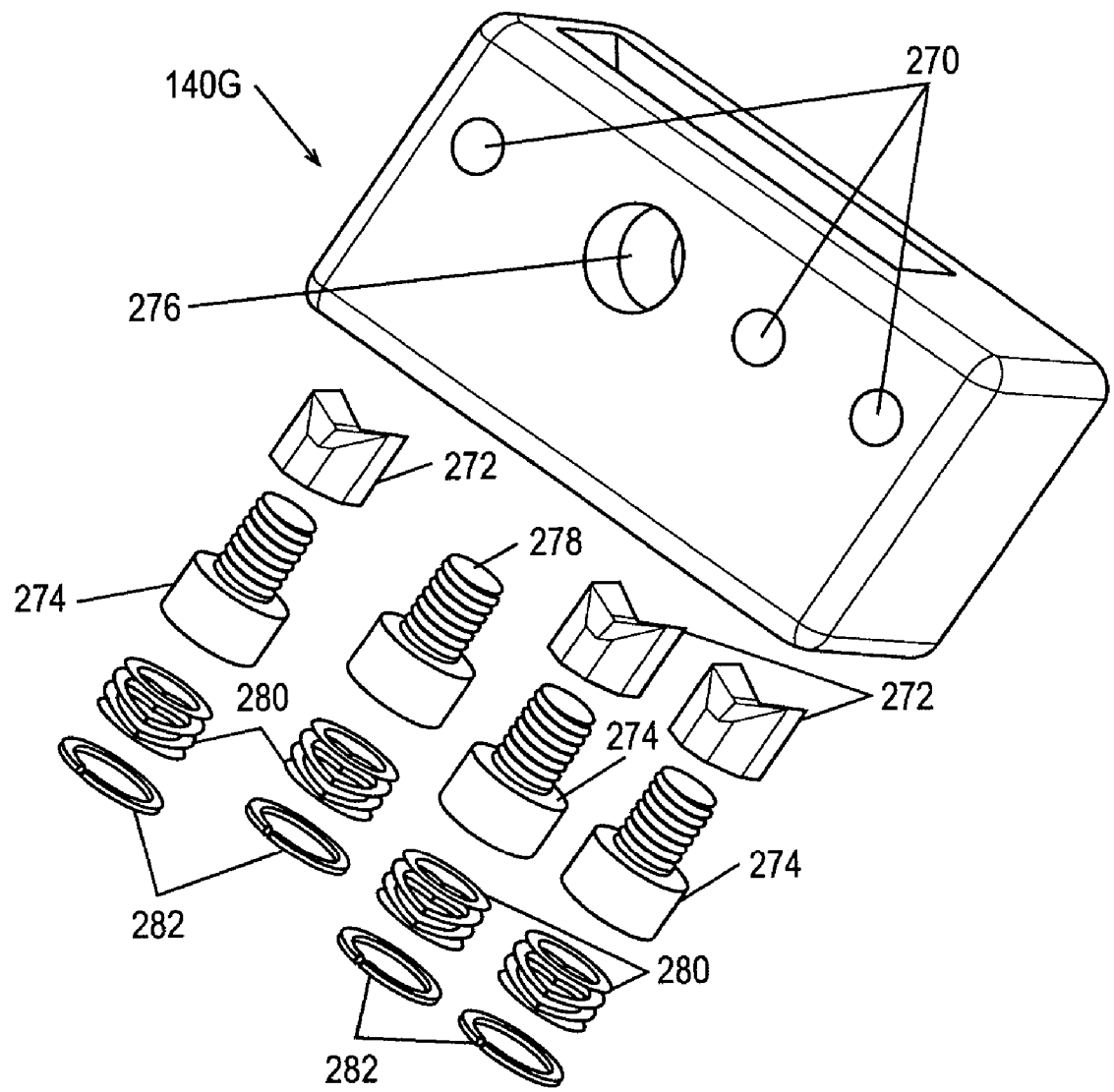
FIG. 12 is a perspective view of an embodiment of a pin clamp according to the present invention.

FIG. 12 is a perspective view of another embodiment of a pin clamp according to the present invention. Unitary body pin clamp 140G may be coupled to either a bifurcated second member (e.g., see FIG. 5), or a unitary second member (e.g., see FIG. 4). Additionally, unitary body pin clamp 140G may be asymmetrical as depicted, or symmetrical with a pin hole 270 configuration similar to that of pin block 140, as shown in FIG. 3. Clamps 272 may be urged by clamp bolts 274 against bone pins in pin holes 270 to attach bone pins to unitary body pin clamp 140G. Pin clamp 140G includes a hole 276 for accepting an axle such as axle 112 shown in FIG. 3. A lock bolt 278 may be used to engage an axle and lock pin clamp 140G relative to the axle. Each of bolts 274 and 278 is held in pin clamp 140G by a bolt spring 280 and a block retainer 282.

Figure 13:
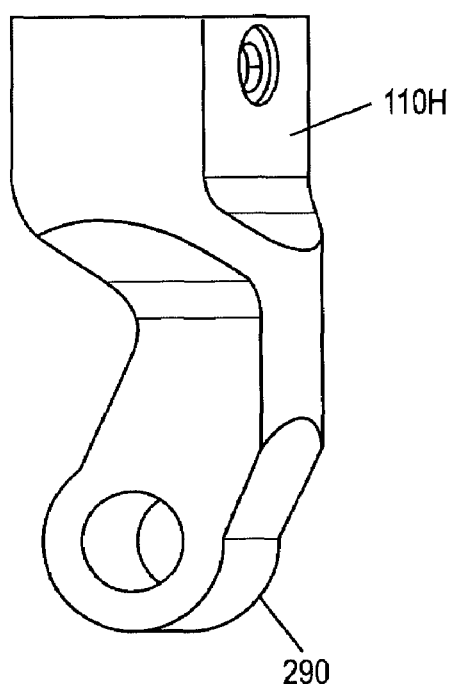
FIG. 13 is a perspective view of an embodiment of a second member according to the present invention configured to create an angular bias from normal between the longitudinal axis of the second member and a pin clamp.
Figure 14:
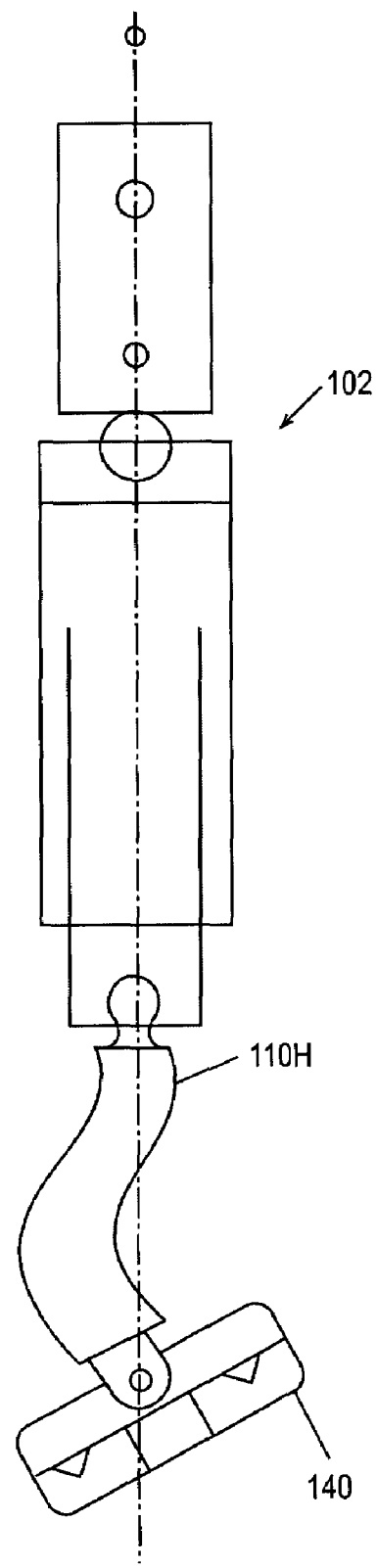
FIG. 14 is a perspective view of an embodiment of an apparatus according to the present invention configured to create an angular bias from normal between the longitudinal axis of the external fixation apparatus and a pin clamp of the apparatus.

FIG. 13 is a perspective view of an embodiment of a second member according to the present invention configured to create an angular bias from normal between the longitudinal axis of the second member and a pin clamp. FIG. 13 shows a biased second member 110H that is biased at its distal end 290 from the member's longitudinal axis by approximately 26 degrees. This bias is useful because it approximates the typical bias from horizontal defined by a line between the locations in the talus and calcaneus where bone pins are typically placed. Therefore, by biasing second member 110H, the fullest range of rotational adjustment in either direction is left for an attached pin clamp. Such a bias makes the need for a notch, such as notch 128 shown in FIG. 3, to provide for additional rotational freedom of the pin clamp less necessary. FIG. 14 is a perspective view of an embodiment of an apparatus according to the present invention configured to create an angular bias from normal between the longitudinal axis of the external fixation apparatus and a pin clamp of the apparatus. Biased second member 110H may be used with a bifurcated or unitary appendage extending from a second member to a pin clamp. The bias may be advantageous if different than 26 degrees. For example, biases in the range of 1 degree to 60 degrees may be useful in certain exemplary embodiments according to the present invention.

Figure 15:
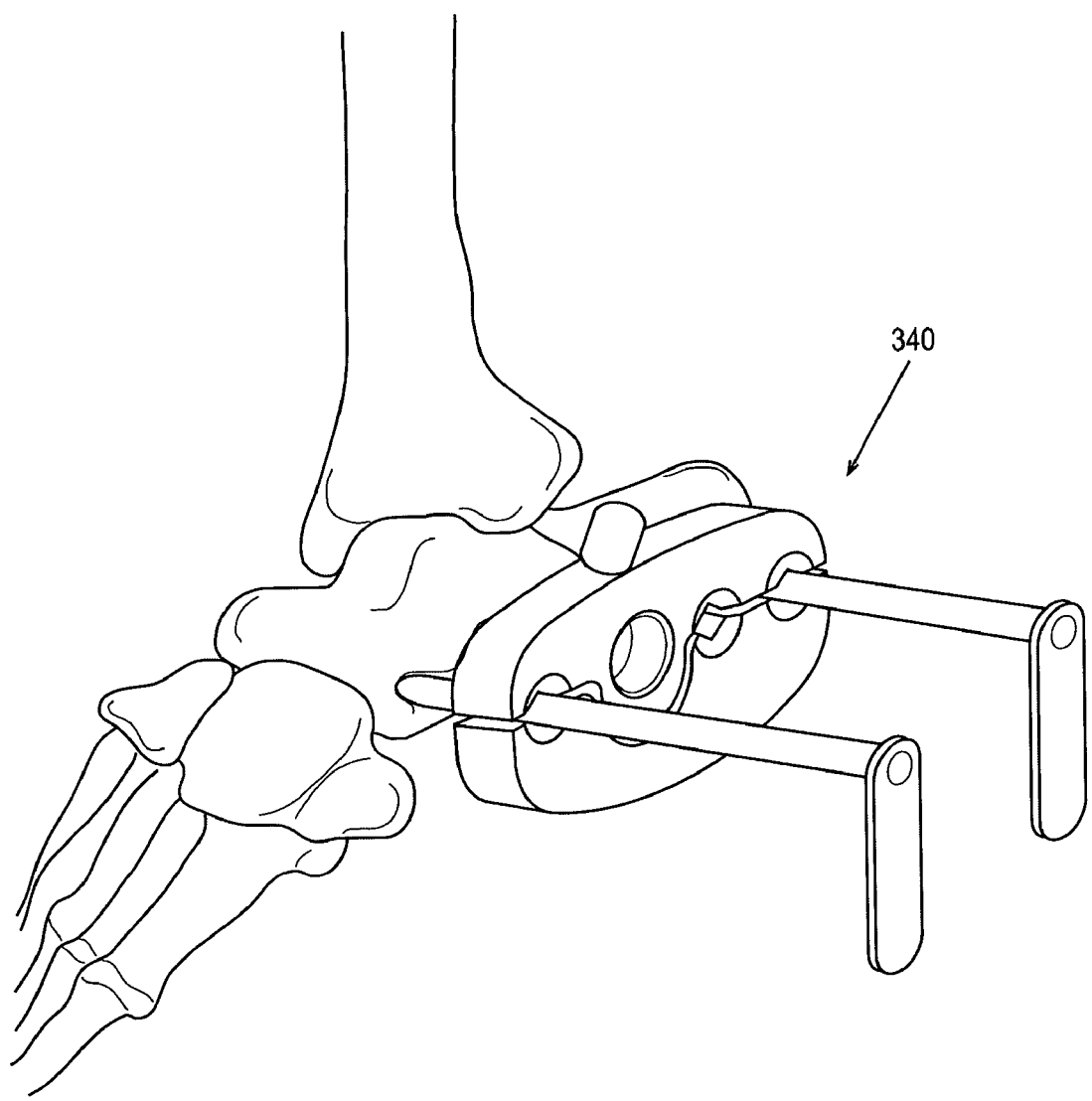
FIG. 15 is a perspective view of an embodiment of a pin clamp according to the present invention over the ankle of a patient with two drill sleeves inserted in the pin clamp.
Figure 16:
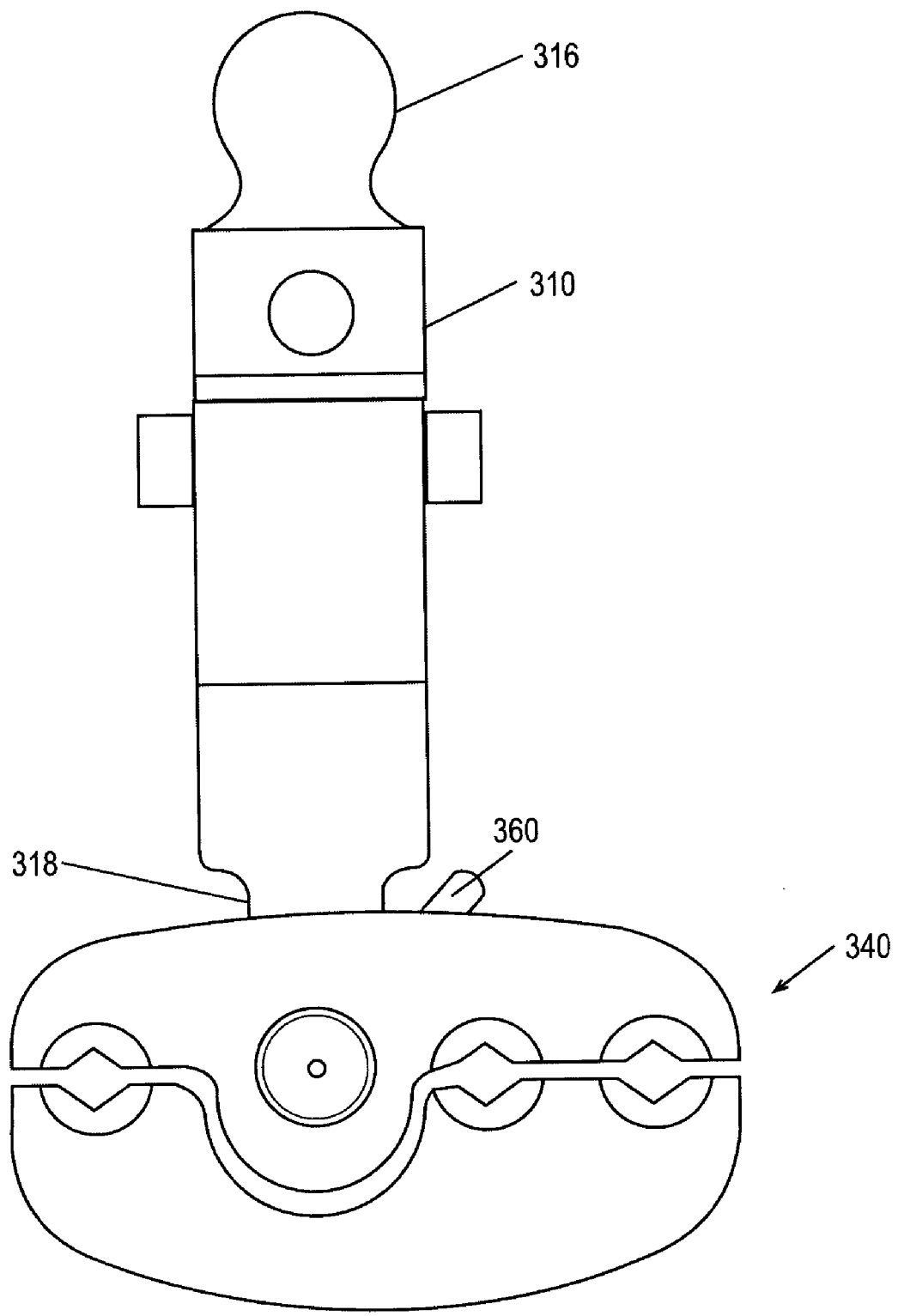
FIG. 16 is an elevation view of an embodiment of an external fixation apparatus according to the present invention including the pin clamp of FIG. 15 and a second member.
Figure 11:
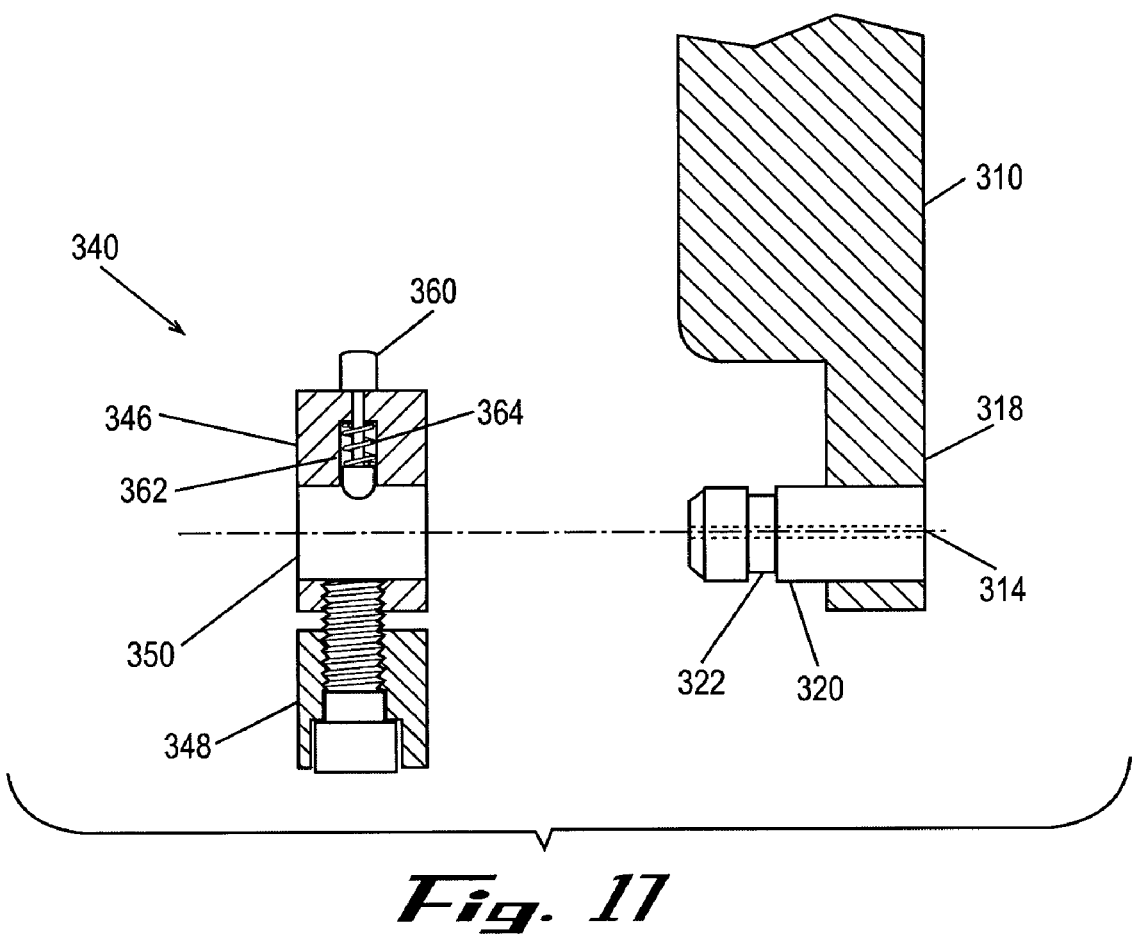
Figure 18:
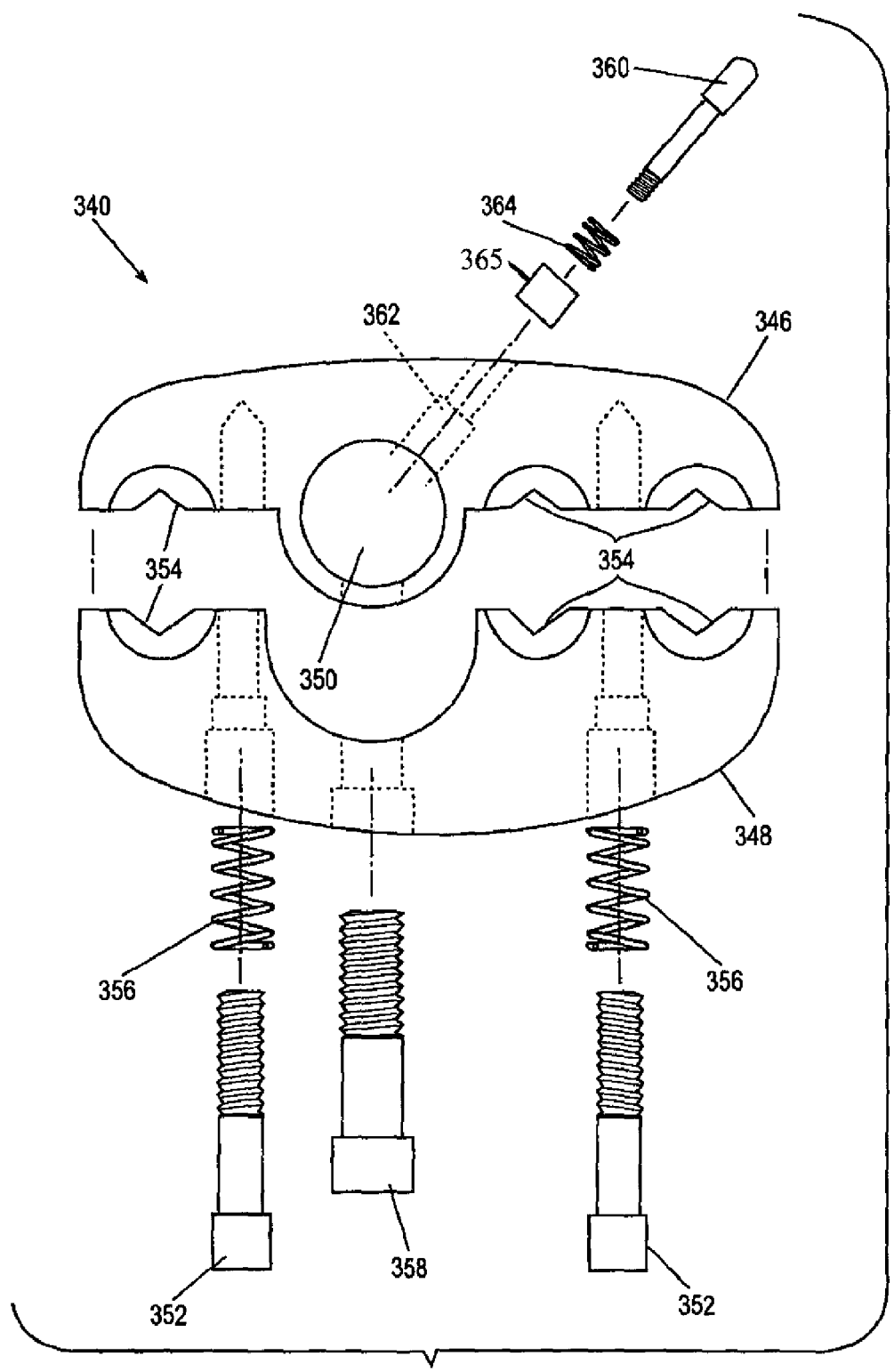
FIG. 18 is an exploded elevation view of the pin clamp shown in FIGS. 15-17.

FIGS. 15-18 show another embodiment of an external fixation apparatus according to the present invention. FIG. 15 shows an embodiment of a pin clamp according to this invention over the ankle of a patient with two drill sleeves inserted in the pin clamp. FIG. 16 shows an elevation view of an embodiment of an external fixation apparatus according to this invention, including the pin clamp of FIG. 15 and a second member. FIG. 17 shows an exploded cross-sectional elevation view of the embodiment of the external fixation apparatus shown in FIG. 16. FIG. 18 shows an exploded elevation view of the pin clamp of FIGS. 15-17.

Referring now to FIGS. 15-18 and more specifically to FIGS. 16-18, this embodiment of an external fixation apparatus provides for releasable engagement of a second member 310 and a pin clamp 340. Pin clamp 340 may be pivoted about the second member 310 and used interchangeably from either the left or the right side of the leg of a patient. Second member 310 may be of a number of configurations, such as unilateral, bar connector, handle, or ring connector. As shown in FIGS. 16 and 17, second member 310 includes a unitary stem. Pin clamp 340 and second member 310 are designed such that pin clamp 340 can easily snap onto and be removed from second member 310 using a locator pin 360 in pin clamp 340 as further described below.

Second member 310 includes ends 316 and 318. At end 316 is a ball joint for connection with a first member (not shown) such as first member 102 described above in conjunction with FIG. 1. Second member 310 may be similar to second member 110 in that second member 310 may include a mechanism by which ends 316 and 318 of second member 310 may translate transversely relative to the longitudinal axis of second member 310 in one or more dimensions. For example, second member 310 may include a carriage 130 with worm gears 132A and 132B, threaded holes 134A and 134B, and keybolts 136 and 138 to provide for translation of ends 316 and 318 relative to the longitudinal axis of the second member as described above in conjunction with second member 110.

At end 318 is a single prong that comprises a unitary stem. A shaft 320 extends from end 318, as shown in FIG. 17, transverse to the longitudinal axis of second member 310. Shaft 320 includes at least one circumferential groove 322. Shaft 320 may include an alignment hole 314 through which a pin or wire may be placed into the bone. Such alignment may be useful to approximate a desired center of rotation of pin clamp 340. For example, a wire may be placed through alignment hole 314 and into the talus to approximate the pivot axis of a patient's ankle.

Pin clamp 340 includes a first jaw 346 and a second jaw 348. First jaw 346 has a hole 350 into which shaft 320 of second member 310 may be inserted. Once shaft 320 is inserted within hole 350, first jaw 346 may rotate about shaft 320, and thus, when the first and second jaws are coupled together, pin clamp 340 may rotate about shaft 320. First jaw 346 and second jaw 348 are held together by clamp bolts 352. Clamp bolts 352 may serve to both hold the jaws together and to attach and clamp bone pins (not shown) to a bone segment (e.g., see FIG. 1). Bone pins may be clamped in any of the three openings defined by the six depressions 354, as shown in FIGS. 16 and 18. Clamp bolts 352 may be urged by biasing elements, such as springs 356, such that first jaw 346 and second jaw 348 tend to push together to stay loosely secured to bone pins prior to tightening clamp bolts 352. A lock bolt 358 may be provided to lock the rotation between second member 310 and pin clamp 340. Lock bolt 358 passes through holes in second jaw 348 and first jaw 346 such that by sufficiently tightening lock bolt 358, the distal end of lock bolt 358 interferes with shaft 322 of second member 310 and locks rotation between second member 310 and pin clamp 340. As shown in FIG. 18, the threaded hole with which lock bolt 358 engages is in first jaw 346.

First jaw 346 includes a stepped hole 362 that retains a biasing element, such as a spring 364, locator pin 360, and stop 365. When shaft 320 of second member 310 is fully inserted within hole 350 of pin clamp 340, circumferential groove 322 receives locator pin 360, engaging second member 310 and first jaw 346 of pin clamp 340 while still allowing rotation of pin clamp 340 about shaft 320. To release engagement between second member 310 and pin clamp 340, locator pin 360 is pulled and shaft 320 of second member 310 may easily be removed from hole 350 of first jaw 346.

Figure 19:
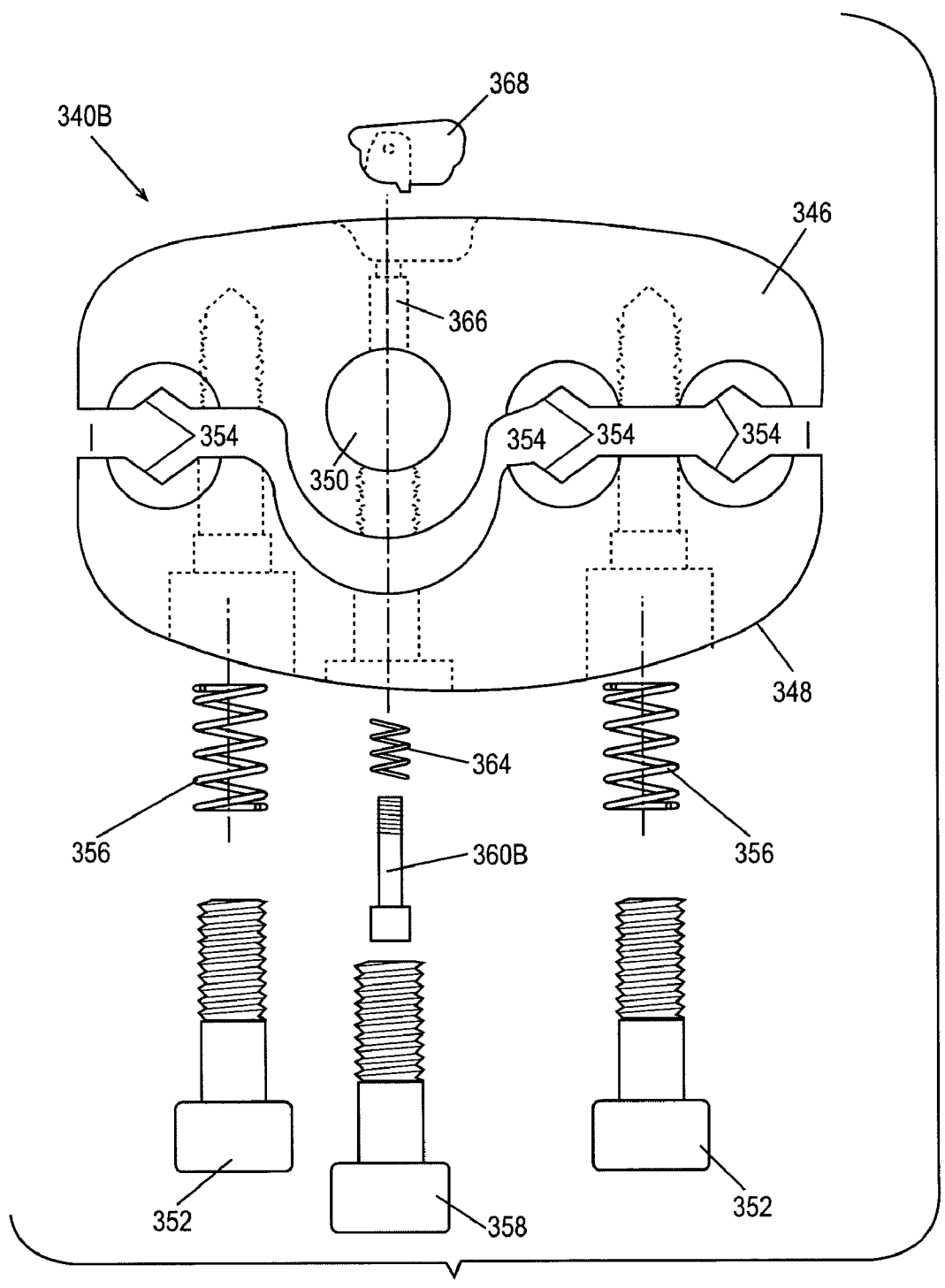
FIG. 19 is an elevation view of another embodiment of a pin clamp with a locator pin according to the present invention.

FIG. 19 shows another exemplary embodiment of a pin clamp with a locator pin according to this invention. Pin clamp 340B is the same as pin clamp 340 shown in FIGS. 15-18 except that the location and configuration of the locator pin assembly has changed. As shown in FIG. 19, locator pin 360B is a pushbutton release mechanism rather than a pull release mechanism. Locator pin 360B and spring 364 are received within a stepped hole 366 in first jaw 346. The proximal tip of locator pin 360B is "pinned" to a button 368 in first jaw 346 in such a way that if you push button 368, locator pin 360B is translated up and out of a mating groove in a hinge shaft (not shown, but an example is shaft 320 with circumferential groove 322 shown in FIGS. 16 and 17) allowing removal of pin clamp 340 from a device with which it was engaged. Spring 364 biases locator pin 360B toward the center of hole 366. As pin clamp 340 is being engaged with shaft 320 with circumferential groove 322, locator pin 360B is forced up, compressing spring 364. The tip of locator pin 360B slides along shaft 320 and then snaps into groove 322 on shaft 320, engaging shaft 320 and pin clamp 340. Pushing button 368 allows for shaft 320 and pin clamp 340 to separated from one another.

Figure 20:
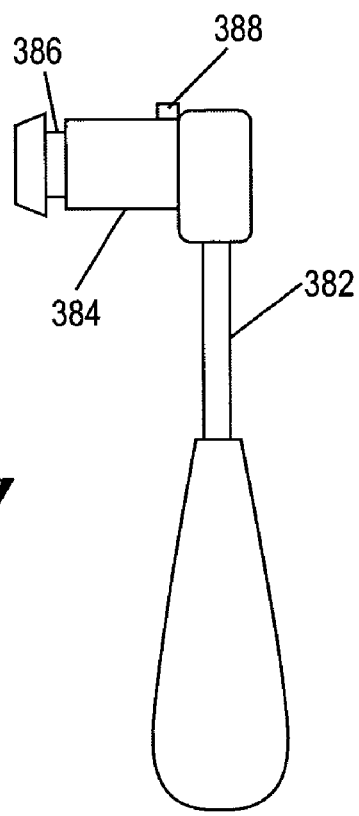
FIG. 20 is an elevation view of an embodiment of a handle assembly for use with an embodiment of a pin clamp according to the present invention.

The embodiments shown and described in FIGS. 15-19 provide for quick and easy reconfiguration of a pin clamp for use with either left or right limb applications, eliminating the need for pin clamps specific to each limb. Additionally, these embodiments allow for quick attachment and removal of second members or stems and pin clamps of external fixation systems. Furthermore, a modular design is provided whereby a pin clamp or second member according to these embodiments may be provided separately from each other and each may be connected with other components, elements, or devices of a fixation system that are similarly designed. For example, the handle assembly shown in FIG. 20 may engage a pin clamp, such as pin clamp 340 or 340B, to form a drill guide for use by a surgeon. A shaft 384 with a circumferential groove 386 extends from one end of a handle 382, as shown in FIG. 20. Shaft 384 may be inserted into a hole of a pin clamp and the locator pin of the pin clamp is received within circumferential groove 386 to engage the handle assembly and the pin clamp. Shaft 384 may also include a key 388 that may engages an opening with a corresponding shape in a pin clamp to assist in aligning the pin clamp with the long axis of handle 382. The engaged handle assembly and pin clamp act as a drill guide, with openings in the pin clamp being able to receive a drill, drill bit, depth gauge, or tissue sleeve used to assist a surgeon in placing a pin, wire, or similar fixation element into a patient's bone.

Figure 21:
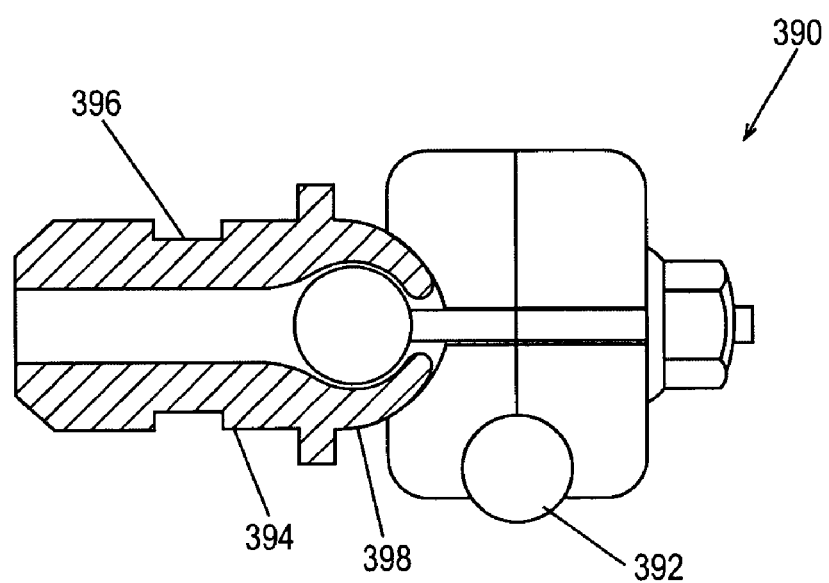
FIG. 21 is an elevation view of an embodiment of a fixation component for use with an embodiment of a pin clamp according to this invention.

In another example, FIG. 21 shows a capture member 390 for receiving a bar 392 of an external fixation system coupled to a shaft 394 with a circumferential groove 396, shaft 394 being designed for engagement with an embodiment of a pin clamp, such as pin clamp 340 or 340B, according to this invention. Capture members, such as capture member 390, for use in external fixation systems are described in detail in U.S. application Ser. No. 10/067,052, filed Feb. 4, 2002, entitled "External Fixation System," and International Application No. PCT/US03/02712, filed Jan. 30, 2003, entitled "External Fixation System," the entire contents of each of which are hereby incorporated by reference. For example, as shown in FIG. 21, an end 398 of shaft 394 may include a generally spherical planetary member having inner and outer surfaces and an aperture adapted to receive a connector, while capture member 390 includes a cooperating surface adapted to receive and correspond generally in shape with the outer surface of the planetary member and an aperture adapted to receive a connector. It should be understood that end 398 of shaft 394 may be formed to mate with capture member 390 according to any of the principles disclosed in the above-referenced, incorporated-by-reference patent applications.

In addition to allowing for a pin clamp to be connected to additional external fixation devices, the embodiments shown in FIGS. 15-19 also allow a second member according to this invention to be connected to various pin clamp configurations, including future versions of pin clamps or custom pin clamps that may be used in an external fixation apparatus or system. Using the connection mechanism shown in these embodiments provides flexibility not afforded by apparatuses where the second member and at least a portion of the pin clamp are permanently affixed or connected to each other.

Certain exemplary embodiments of this invention include methods of reducing a fracture. Certain exemplary embodiments of apparatuses according to this invention offer the unique ability to precisely adjust and thereby precisely reduce a fracture after all of the bone pins are placed and the apparatus is tightened onto the pins. An exemplary embodiment includes fixing a first member to one side of a bone fracture and fixing a second member to a second side of a bone fracture to approximately accomplish reduction of the fracture. Subsequently, adjustments of the members may be performed to precisely reduce the fracture. For example, referring to FIG. 3, keybolts 136 and 138 may be operated to adjust a fracture transversely relative to the longitudinal axis of the second member. All of the adjustments described in association with certain exemplary embodiments of apparatuses of this invention may also be accomplished under certain exemplary embodiments of methods according to this invention. Such adjustments are advantageous because loosening of the main couplings within the device may cause additional fracture misalignment, leading to still further adjustment requirements.

In an exemplary embodiment according to a method of this invention, fixing a first member to one side of a bone fracture is accomplished. Then, the unique adjustment features of certain exemplary embodiments of this invention may be employed to make an advantageous position and orientation alignment of bone pins to a suitable location on the other side of the fracture. Specifically, the multi-axis adjustments available between the first member and the second member and the multi-axis adjustments between the second member and the pin clamp may be used to make an advantageous position and orientation alignment of bone pins. Further, adjustments of the members may be performed to precisely reduce the fracture as noted above.

In another exemplary embodiment, lower bone pins may be placed prior to the placement of any upper bone pins and without the first or second members being attached to the pin clamp. According to one embodiment, lower bone pins may be placed within a pin clamp that releasably connects to a second member and affixed to the bone fracture. Subsequently, a second member may be connected to the pin clamp, followed by a first member with which the upper bone pins are then placed into the bone. This provides added flexibility to a user because the lower bone pins may be placed without the cumbersome first or second members of the external fixation apparatus being attached to the pin clamp, and greater degrees of freedom of the pin clamp are available for optimal placement of the lower bone pins.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope.

What is claimed is:

1. An external fixation apparatus comprising:
   a pivot arm comprising: an upper portion having a first end portion and a second opposite end portion having a first recess formed therein; and a lower portion having a third end portion with a prong end and a fourth opposite end portion having a second recess formed therein, wherein the lower portion and upper portion are secured together with the first and second recesses adjacent one another to form an internal recess in the pivot arm;
   a pin clamp coupled to and rotatable about the prong end of the third end portion, the pin clamp being attachable to a bone segment; and
   a carriage unit located within the internal recess, the carriage unit operatively connected to the upper portion and to the lower portion, and the carriage unit having a first adjustment member for adjustment of at least one portion of the pivot arm in a medial-lateral direction and a second adjustment member for adjustment of at least one portion of the pivot arm in an anterior-posterior direction,
   wherein the first adjustment member and the second adjustment member each comprise a worm gear and a keybolt.

2. The external fixation apparatus of claim 1, wherein the prong end of the lower portion of the pivot arm consists essentially of a single prong.

3. The external fixation apparatus of claim 1, wherein the pin clamp is symmetrical or asymmetrical.

4. The apparatus of claim 1, wherein the pin clamp further comprises a push/pull mechanism having at least one end externally accessible during use for releasably coupling the pin clamp.

5. The external fixation apparatus of claim 1, wherein the first adjustment member is adjustable independently of the second adjustment member.

6. An external fixation system for attaching pins or wires to at least one bone segment, the system comprising:
   a first member;
   a second member coupled to the first member, the second member comprising a shaft that extends transversely from an end portion of the second member and has a groove extending substantially around a circumference of the shaft; and
   a pin clamp attachable to and detachable from the shaft of the second member, the pin clamp comprising:
      a first jaw and a second jaw, the first jaw having a central portion and two opposed jutting portions, the central portion having a bore adapted to receive the shaft and a hole located transverse to the bore; and
      a release mechanism that is positioned within the first jaw and is externally accessible for manual manipulation during use of the pin clamp, the release mechanism comprising a locator pin, a stop connected to the locator pin and located within the hole, and a biasing element, wherein the biasing element is adapted to bias the stop toward the groove when the second member and the pin clamp are coupled.

7. The system of claim 6, wherein the second member has at least one other end portion and the end portions may be translated transversely relative to a longitudinal axis of the second member in at least two dimensions.

8. The system of claim 6, wherein the locator pin is pulled manually by the user to allow for release of the shaft from the pin clamp.

9. The system of claim 6, wherein the pin clamp further comprises:
   openings in each of the first and second jaws; and
   biasing elements received within the openings, the biasing elements adapted to bias the first and second jaws toward each other.

10. The system of claim 9, wherein the pin clamp further comprises first and second bolts that extend into the openings in the first and second jaws, the first and second bolts configured to compress the biasing elements and hold the first and second jaws together.

11. The system of claim 6, wherein the locator pin further comprises an enlarged knob end that is manually pulled to remove an opposite end of the locator pin from the groove of the shaft.

12. The system of claim 6, wherein the pin clamp snap fits onto the shaft of the second member.

13. A method of treating a skeletal condition or injury using an external fixation apparatus, the method comprising:
   (a) fixing a first member to a first side of a fracture with upper bone pins;
   (b) fixing a pin clamp to a second side of the fracture with lower bone pins;
   (c) providing a pivot arm comprising an upper portion with a ball end and a second end opposite the ball end with a first recess formed in the second end and a lower portion with a prong end and a second end opposite the prong end with a second recess formed in the second end, where the upper and lower portions are secured together with the first and second recesses adjacent one another to form an internal recess in the pivot arm;
   (d) coupling the pin clamp to the first member through the use of the pivot arm, wherein the lower portion of the pivot arm is coupled directly to the pin clamp;
   (e) moving a carriage that is within the internal recess of the pivot arm to adjust a position of one of the upper and lower portions of the pivot arm with respect to a longitudinal axis of the pivot arm in an anterior-posterior direction; and (f) moving the carriage that is within the internal recess of the pivot arm to adjust a position of one of the upper and lower portions of the pivot arm with respect to a longitudinal axis of the pivot arm in a medial-lateral direction.

14. The method of claim 13, further comprising rotating the pin clamp as desired for placement of the lower bone pins.

15. The method of claim 13, wherein the pin clamp is fixed prior to the fixing of the first member.

16. An external fixation apparatus comprising:
a pivot arm having an upper portion and a lower portion;
a shaft connected to the lower portion, the shaft having a circumferential grove;
a pin clamp removably attached to the shaft, the pin clamp comprising a first jaw and a second jaw, the first jaw having a central portion and two opposed jutting portions, the central portion having a bore adapted to receive the shaft and a stepped hole located transverse to the bore;
a stop located within the stepped hole, the stop adapted to slide within the stepped hole and selectively engage the circumferential groove;
a biasing element placed within the stepped hole to bias the stop into positive engagement with the circumferential groove; and
a locator pin connected to the stop for selective movement of the stop out of contact with the groove.

17. An external fixation apparatus comprising:
a pivot arm having an upper portion, a lower portion, and an internal recess;
a shaft connected to the lower portion, the shaft having a circumferential grove;
a pin clamp removably attached to the shaft of the second member, the pin clamp comprising a first jaw and a second jaw, the first jaw having a central portion and two opposed jutting portions, the central portion having a bore adapted to receive the shaft and a stepped hole located transverse to the bore;
a stop located within the stepped hole, the stop adapted to slide within the stepped hole and selectively engage the circumferential groove;
a biasing element placed within the stepped hole to bias the stop into positive engagement with the circumferential groove;
a locator pin connected to the stop for selective movement of the stop out of contact with the groove; and
a carriage unit located within the recess, the carriage unit operatively connected to the upper portion and to the lower portion, and the carriage unit having a first adjustment member for adjustment of at least one portion of the pivot arm in a medial-lateral direction and a second adjustment member for adjustment of at least one portion of the pivot arm in an anterior-posterior direction.

18. An external fixation apparatus comprising:
a pivot arm having an upper portion and a lower portion, the upper portion having a first end portion and a second opposite end portion having a first recess formed therein; and the lower portion having a third end portion with a prong end and a fourth opposite end portion having a second recess formed therein, wherein the lower portion and upper portion are secured together with the first and second recesses adjacent one another to form an internal recess in the pivot arm;
a pin clamp removably attached to the lower portion; and
a carriage within the internal recess, the carriage comprising a first worm gear, a second worm gear, a first keybolt corresponding to the first worm gear, and a second keybolt corresponding to the second keybolt, wherein the upper portion may be translated relative to the lower portion in at least two independent directions.

19. An external fixation apparatus comprising:
a pivot arm having a longitudinal axis, an upper portion and a lower portion, the upper portion having a ball end and a second opposite end having a first recess formed therein, the lower portion with a prong end and a second opposite end having a recess formed therein, wherein the lower portion and upper portion are secured together with the first and second recesses adjacent one another to form an internal recess in the pivot arm;
a carriage within the internal recess, the carriage comprising a first worm gear, a second worm gear, a first keybolt corresponding to the first worm gear, and a second keybolt corresponding to the second keybolt, wherein rotation of the first keybolt moves the lower portion in a medial-lateral direction and rotation of the second keybolt moves the upper portion in an anterior-posterior direction;
a shaft connected to the prong end, the shaft having a circumferential grove;
a pin clamp removably attached to the shaft of the second member, the pin clamp comprising a first jaw and a second jaw, the first jaw having a central portion and two opposed jutting portions, the central portion having a bore adapted to receive the shaft and a stepped hole located transverse to the bore;
a stop located within the stepped hole, the stop adapted to slide within the stepped hole and selectively engage the circumferential groove;
a biasing element placed within the stepped hole to bias the stop into positive engagement with the circumferential groove; and
a locator pin connected to the stop for selective movement of the stop out of contact with the groove.

* * * * *

UNITED STATES PATENT AND TRADEMARK OFFICE
CERTIFICATE OF CORRECTION

PATENT NO.      : 7,608,074 B2                                        Page 1 of 1
APPLICATION NO. : 10/607010
DATED           : October 27, 2009
INVENTOR(S)     : Austin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 499 days.

Signed and Sealed this

Twelfth Day of October, 2010

David J. Kappos
*Director of the United States Patent and Trademark Office*